US011511118B2

(12) United States Patent
Atwater et al.

(10) Patent No.: US 11,511,118 B2
(45) Date of Patent: Nov. 29, 2022

(54) SYSTEMS AND METHODS FOR SELECTING, POSITIONING, AND CONTROLLING CARDIAC RESYNCHRONIZATION THERAPY (CRT) ELECTRODES

(71) Applicant: Duke University, Durham, NC (US)

(72) Inventors: Brett Atwater, Durham, NC (US); Daniel Friedman, Durham, NC (US)

(73) Assignee: Duke University, Durham, NC (US)

(*) Notice: Subject to any disclaimer, the term of this patent is extended or adjusted under 35 U.S.C. 154(b) by 297 days.

(21) Appl. No.: 16/786,975

(22) Filed: Feb. 10, 2020

(65) Prior Publication Data

US 2020/0254248 A1 Aug. 13, 2020

Related U.S. Application Data

(60) Provisional application No. 62/803,638, filed on Feb. 11, 2019.

(51) Int. Cl.
*A61N 1/36* (2006.01)
*A61N 1/365* (2006.01)
(Continued)

(52) U.S. Cl.
CPC ............. *A61N 1/365* (2013.01); *A61N 1/368* (2013.01); *A61N 1/39622* (2017.08); *A61N 1/056* (2013.01)

(58) Field of Classification Search
CPC .... A61N 1/365; A61N 1/368; A61N 1/39622; A61N 1/056; A61N 1/3686
See application file for complete search history.

(56) References Cited

U.S. PATENT DOCUMENTS 9,662,499 B2 5/2017 Atwater
2006/0271121 A1 11/2006 Ding et al.
(Continued)

FOREIGN PATENT DOCUMENTS

CA 2898254 A1 7/2014

OTHER PUBLICATIONS

Emerek, K. et al., Vectorcardiographic QRS Area is Associated with Long-Term Outcome Following Cardiac Resynchronization Therapy, Heart Rhythm, Feb. 2019, 213-219, 16(2), Elsevier, Amsterdam.
(Continued)

*Primary Examiner* — Rex R Holmes
(74) *Attorney, Agent, or Firm* — Olive Law Group, PLLC

(57) ABSTRACT

Systems and methods for selecting, positioning, and controlling cardiac resynchronization therapy (CRT) electrodes are disclosed. According to an aspect, a CRT system includes one or more electrodes configured to be positioned on or in proximity to a subject's heart for receiving electrical signals carrying EGM data. The system also includes a CRT device operatively connected to the electrode(s). The CRT device is configured to receive the electrical signals from the electrode(s) when the one or more electrodes are positioned in a first arrangement with respect to the subject's heart. Further, the CRT device is configured to determine a second arrangement of the electrode(s) with respect to the subject's heart based on the carried EGM data. The CRT device is configured to present the second arrangement of the electrode(s).

11 Claims, 15 Drawing Sheets

(51) Int. Cl.
    *A61N 1/39*     (2006.01)
    *A61N 1/368*     (2006.01)
    *A61N 1/05*     (2006.01)

(56) References Cited

U.S. PATENT DOCUMENTS

2015/0032171 A1* 1/2015 Ghosh .................. A61B 5/287
                                                          607/18
2017/0340887 A1* 11/2017 Engels .................. A61B 5/366

OTHER PUBLICATIONS

Friedman, D. et al., Non-Invasively Quantified Changes in Left Ventricular Activation Predict Outcomes in Patients Undergoing Cardiac Resynchronization Therapy, Journal of Cardiovascular Electrophsiology, Nov. 2019, 2475-2483, 30(11), Wiley, Hoboken, NJ.

Okafor, O. et al., Changes in QRS Area and QRS Duration After Cardiac Resynchronization Therapy Predict Cardiac Mortality, Heart Failure Hospitalizations, and Ventricular Arrhythmias, Journal of the American Heart Association, Oct. 28, 2019, 1-16, 8 (21), American Heart Association Inc., Dallas.

Rad, M.M. et al., Vectorcardiographic QRS area identifies delayed left ventricular lateral wall activation determined by electroanatomic mapping in candidates for cardiac resynchronization therapy, Heart Rhythm, Jan. 2016, 217-225, 13(1), Elsevier, Amsterdam.

Van Stipdok, A. et al., QRS Area Is a Strong Determinant of Outcome in Cardiac Resynchronization Therapy, Circulation: Arrhythmia and Electrophysiology, Dec. 13, 2018, 1-11, 11, American Heart Association, Inc., Dallas.

* cited by examiner

Paced EGM     Native EGM

SYSTEMS AND METHODS FOR SELECTING, POSITIONING, AND CONTROLLING CARDIAC RESYNCHRONIZATION THERAPY (CRT) ELECTRODES

CROSS REFERENCE TO RELATED APPLICATION

This application claims priority to U.S. Provisional Patent Application No. 62/803,638, filed Feb. 11, 2019, and titled SYSTEMS AND METHODS FOR IDENTIFYING OPTIMAL CHANGES IN LEFT VENTRICULAR ACTIVATION DURING CARDIAC RESYNCHRONIZATION THERAPY, the content of which is incorporated herein by reference in its entirety.

TECHNICAL FIELD

The presently disclosed subject matter relates generally to medical devices and techniques. Particularly, the presently disclosed subject matter relates to systems and methods for selecting, positioning, and controlling cardiac resynchronization therapy electrodes.

BACKGROUND

Heart failure (HF) currently affects about 5.2 million Americans (2.5% of the total U.S. population) with 550,000 new cases diagnosed each year. The high cost is driven largely by frequent hospital admissions for poorly controlled symptoms. Among patients over age 65, HF is the leading cause of hospitalization, followed by pneumonia, cerebrovascular disease, cancer, and coronary atherosclerosis. An urgency to improve our understanding of HF and to develop new treatment modalities results from the rapidly rising incidence of HF. Cardiac dyssynchrony is present in a substantial proportion of patients with HF and usually manifests as prolongation of the QRS interval on surface electrocardiogram.

Cardiac resynchronization therapy (CRT) can restore synchronous LV contraction in some patients with dyssynchrony. CRT is a well-established therapy for patients with systolic heart failure and evidence of electrical dyssynchrony on the 12-lead electrocardiogram (ECG). Successful electrical resynchronization reduces overall left ventricular (LV) activation delays and is associated with improvements in LV structure and function, affording improvements in HF, quality of life, and survival. Optimal changes in LV activation after CRT improve survival but can be difficult to quantify rapidly, non-invasively and in a continuous manner. Hence, there is a need for the automatic and ongoing CRT optimization for the individual patient being treated (e.g., personalized CRT) as well as to guide optimal lead location during implantation procedures.

BRIEF DESCRIPTION OF THE DRAWINGS

Figure 1:
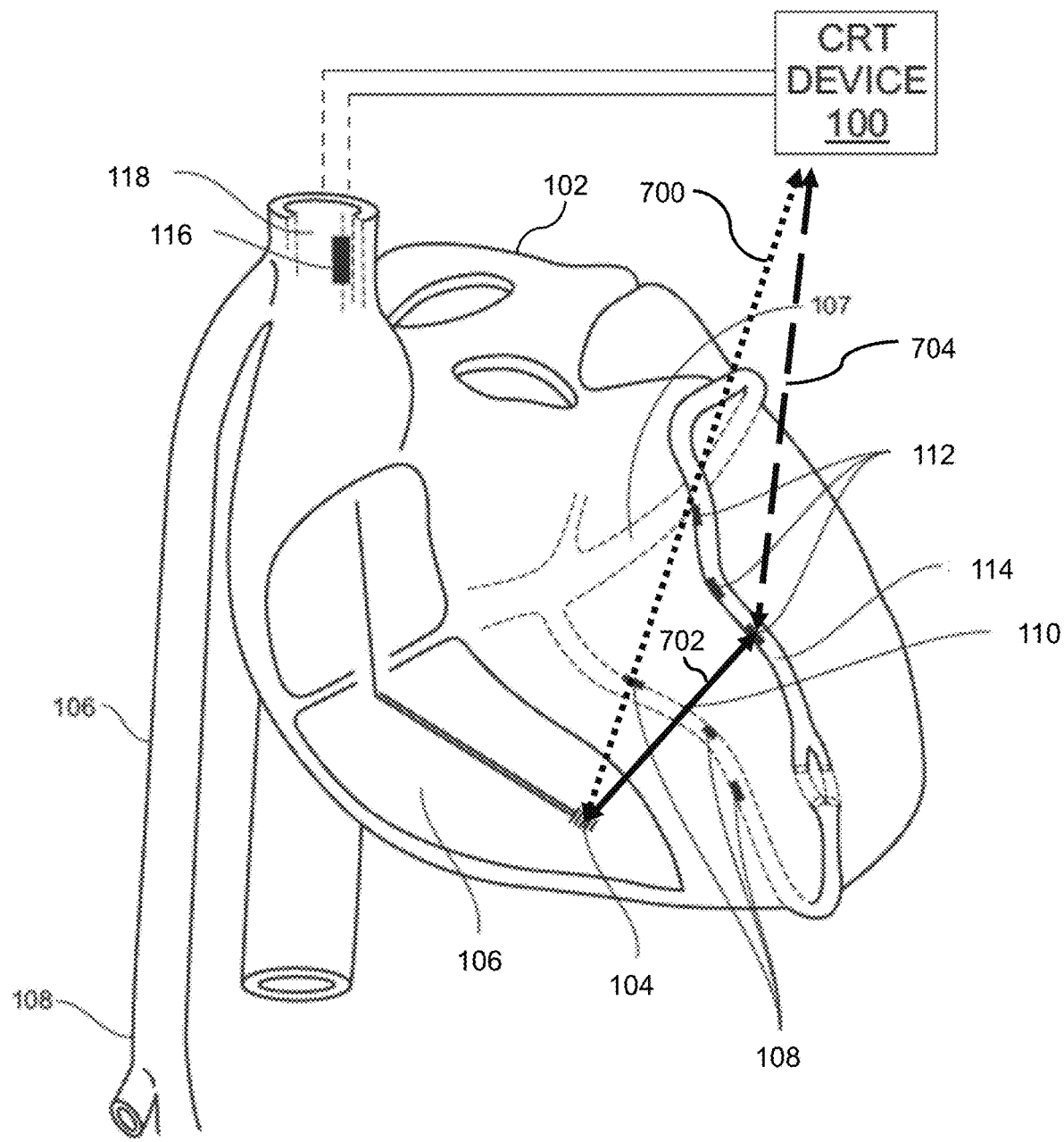
Figure 2:
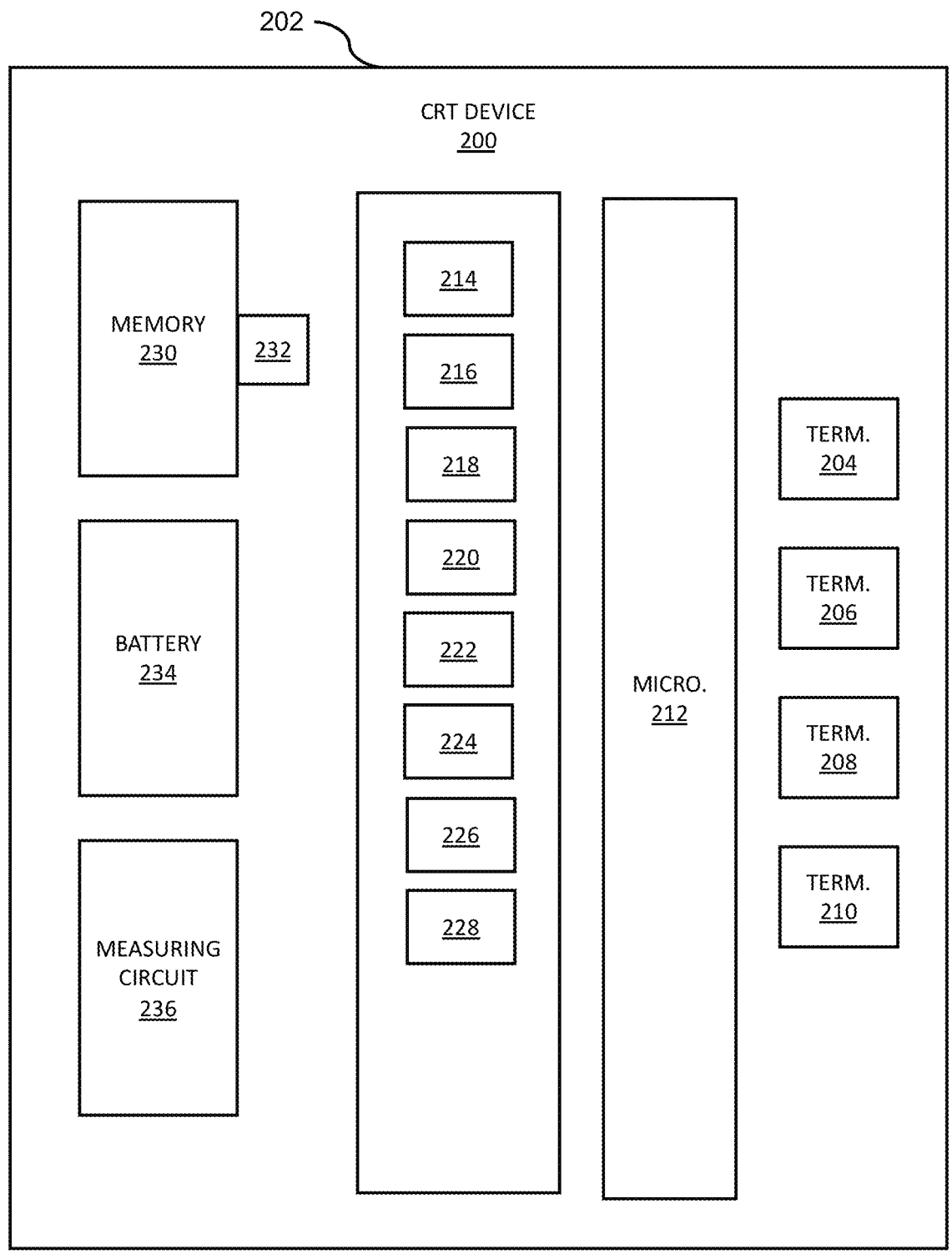
Figure 3:
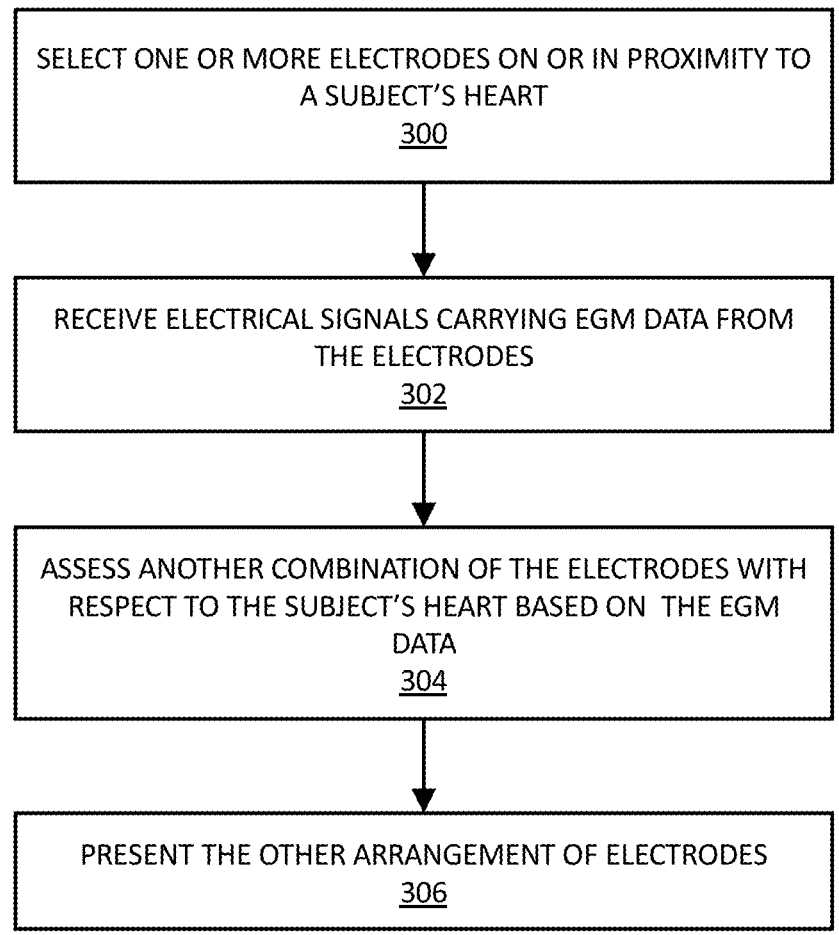
Figure 4:
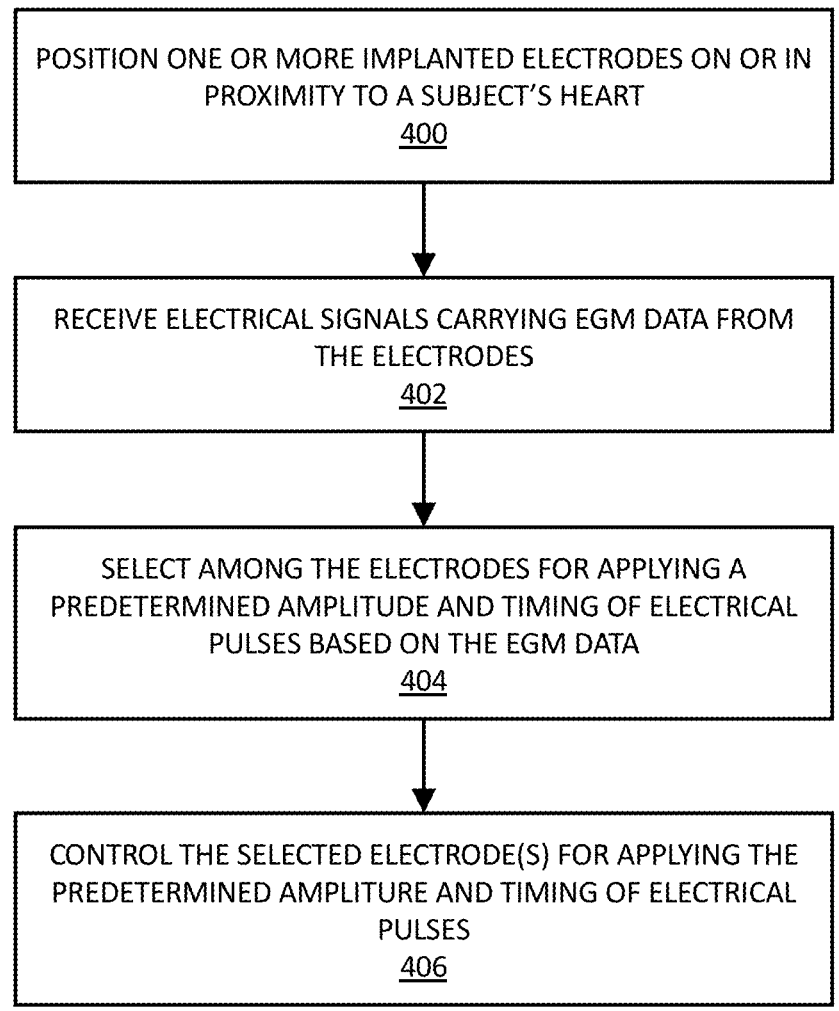
Figure 5:
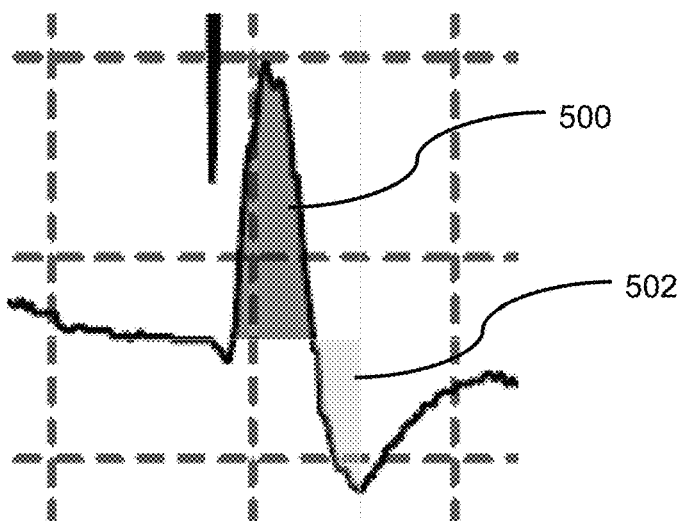
Figure 6:
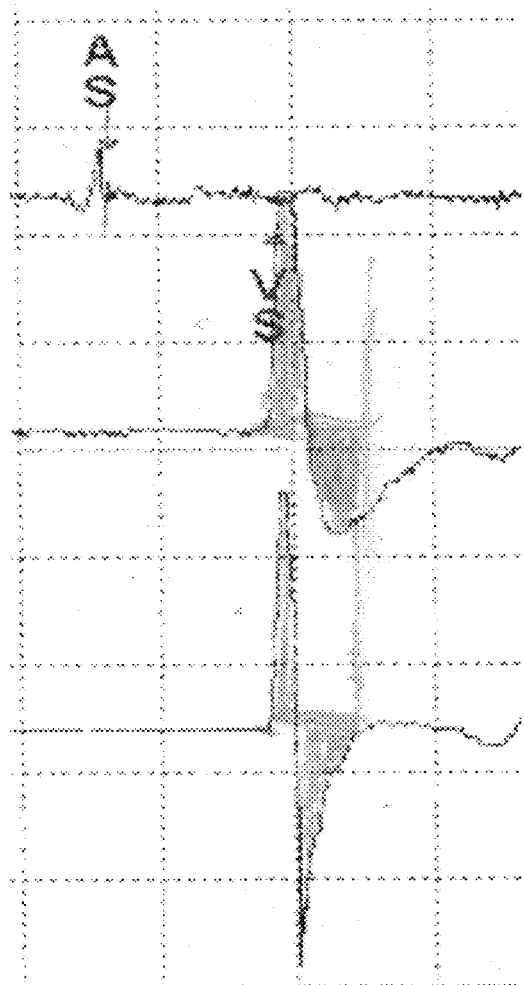

Having thus described the presently disclosed subject matter in general terms, reference will now be made to the accompanying Drawings, which are not necessarily drawn to scale, and wherein:

FIG. 1 is a diagram of an exemplary system including a CRT device in electrical communication with a patient's heart by way of various electrodes positioned for delivering heart stimulation and shock therapy in accordance with embodiments of the present disclosure;

FIG. 2 is a block diagram depicting various example components of a CRT device in accordance with embodiments of the present disclosure;

FIG. 3 is a flow chart of an exemplary method for determining an arrangement of electrodes of a CRT system with respect to a patient's heart in accordance with embodiments of the present disclosure;

FIG. 4 is a flow chart of an exemplary method for selecting CRT device electrodes and their electrical pulse amplitude and timing for application to a patient's heart in accordance with embodiments of the present disclosure;

FIG. 5 is a graph showing the EGM area measured from the RV coil to Can intracardiac electrogram (EGM) signal;

FIG. 6 is a graph showing EGM areas measured in the RV coil to Can EGM signal (top) and the LV electrode to RV coil configuration (bottom).

Figure 7:
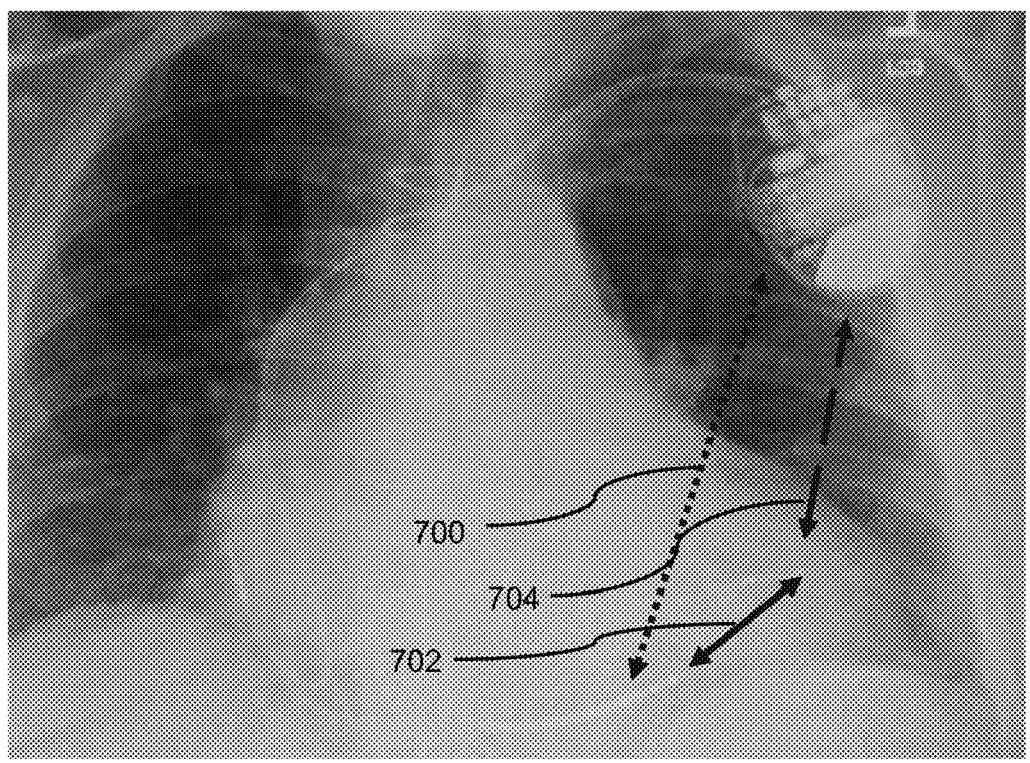
Figure 8:
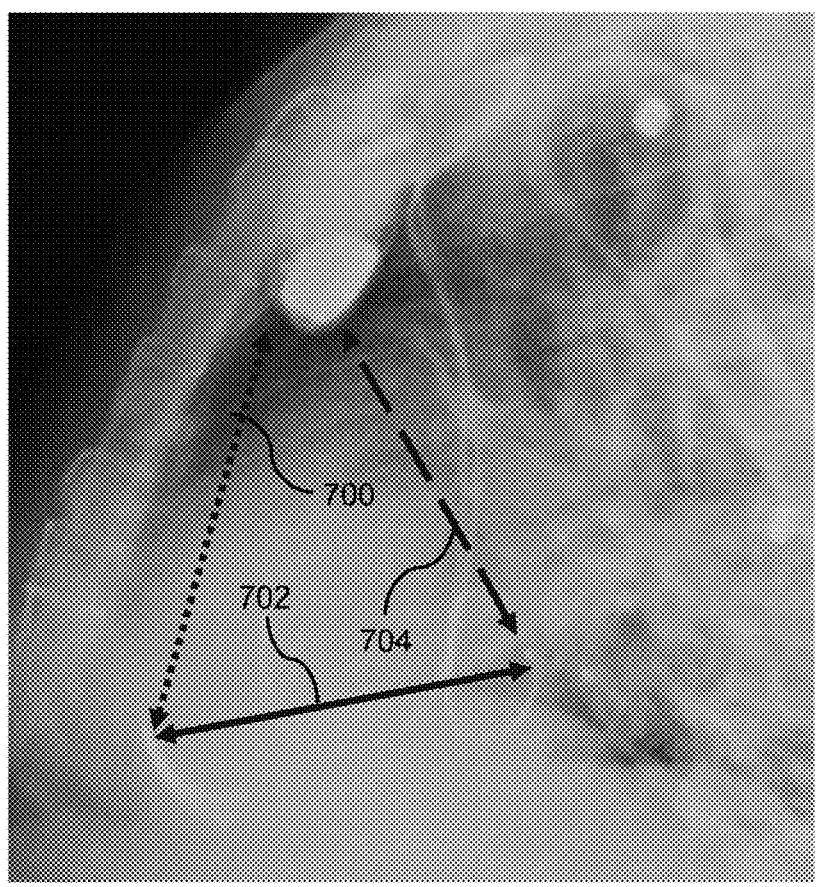
Figure 9:
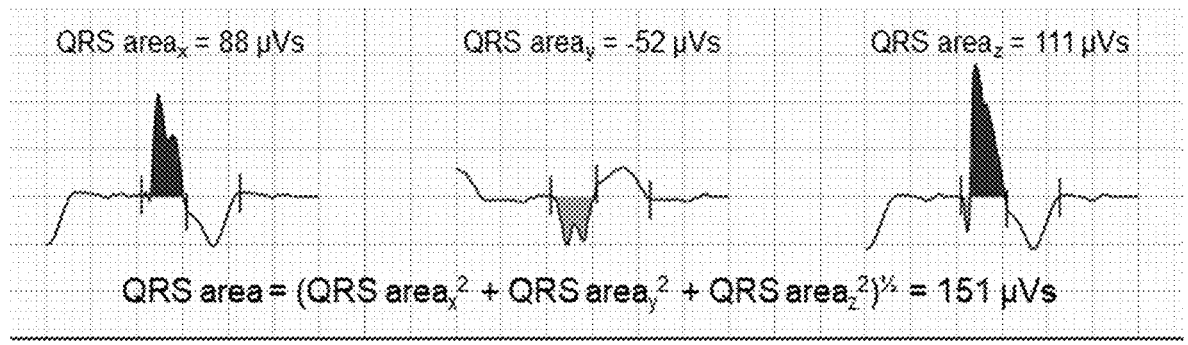
Figure 10:
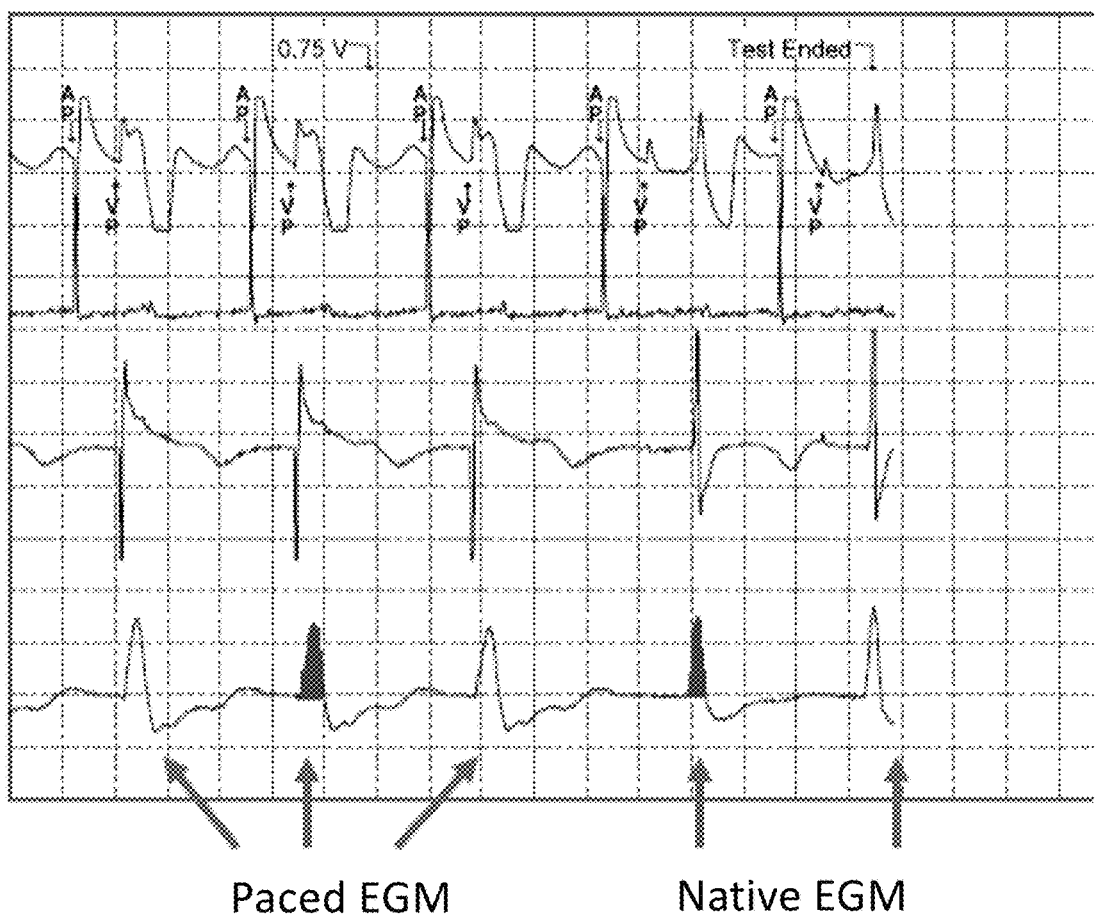
Figure 11:
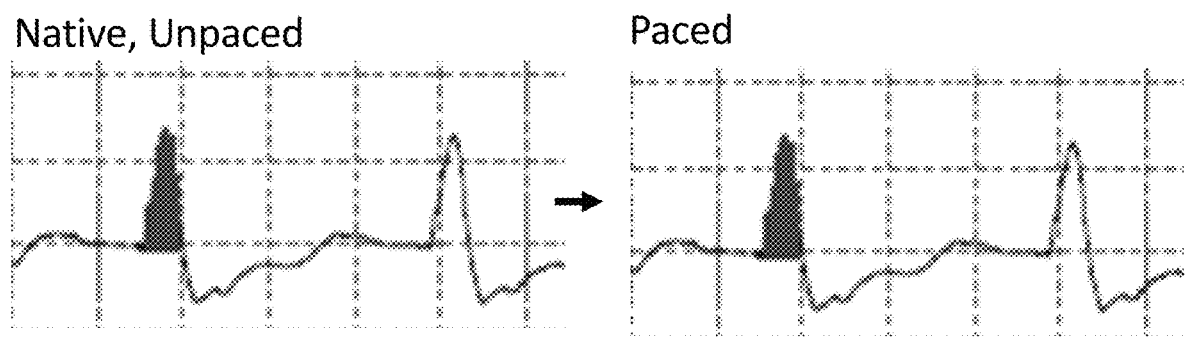
Figure 12:
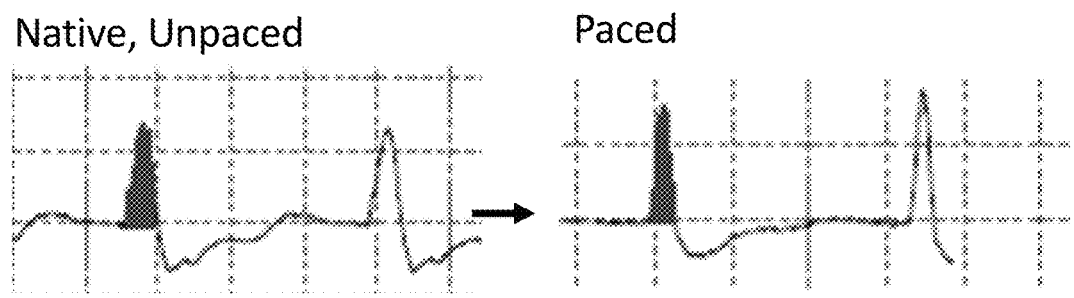
Figure 14:
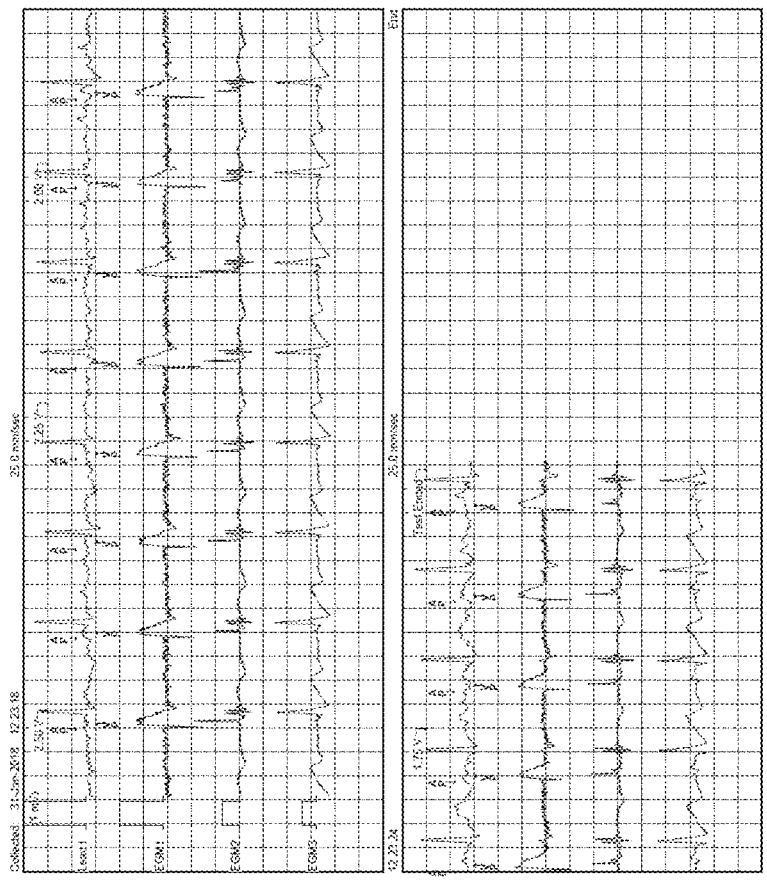
Figure 13:
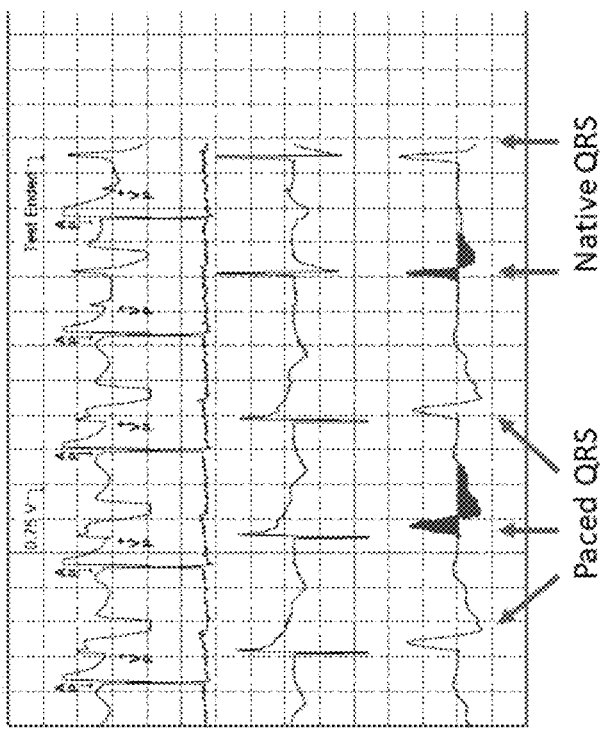
Figure 15:
Figure 16:
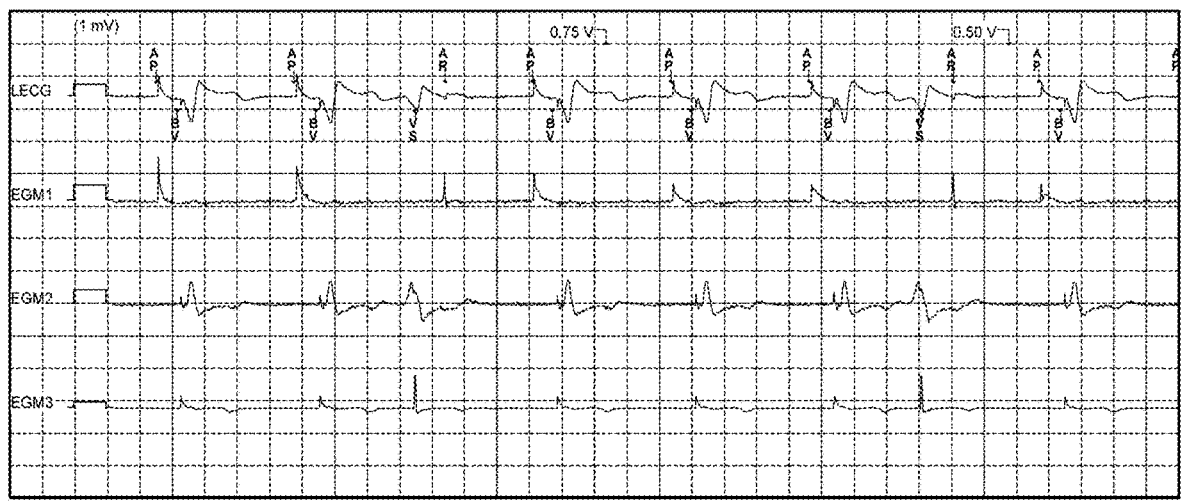
Figure 17:
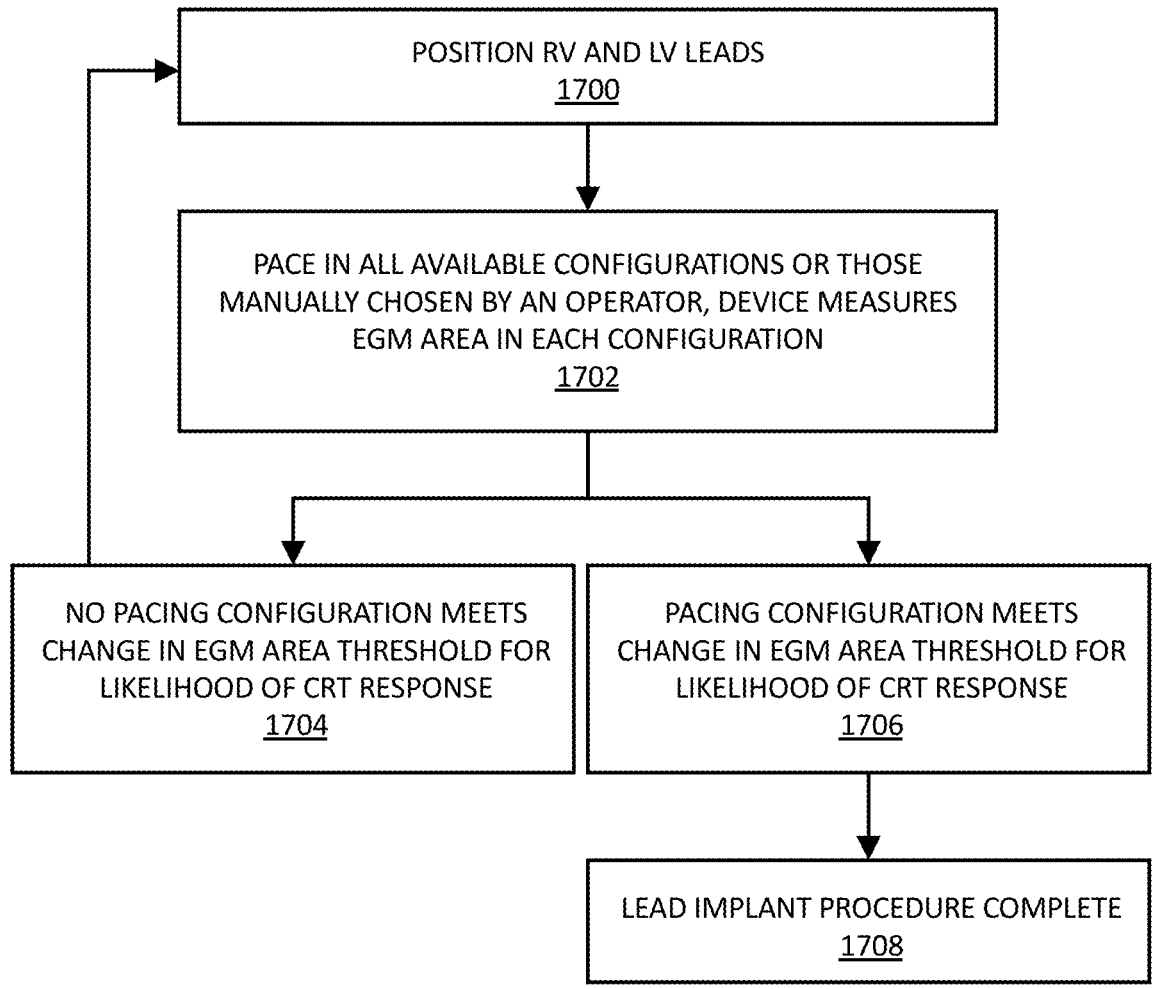
Figure 18:
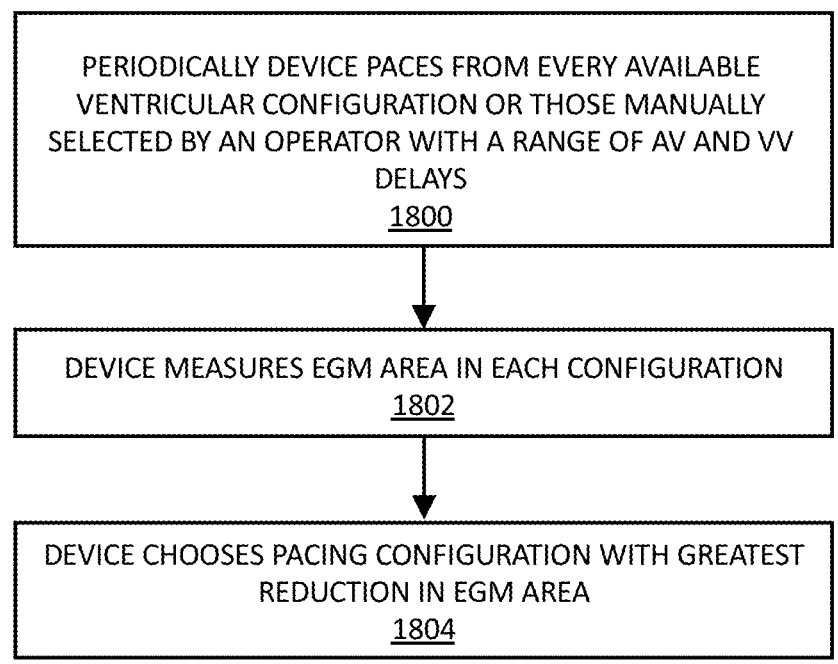
Figure 19:
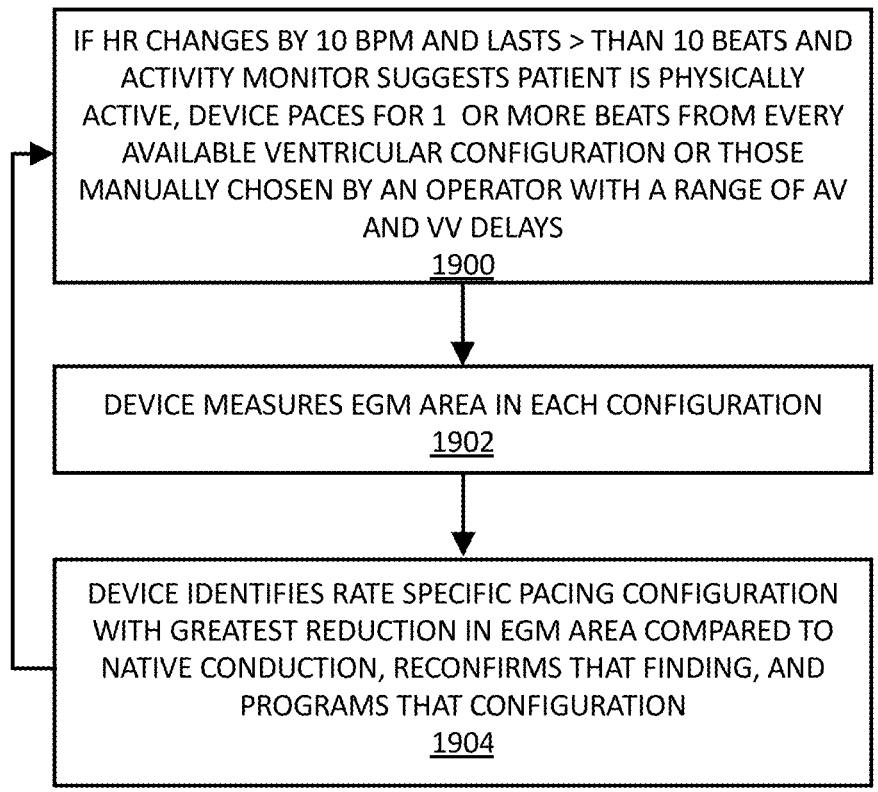
Figure 20:
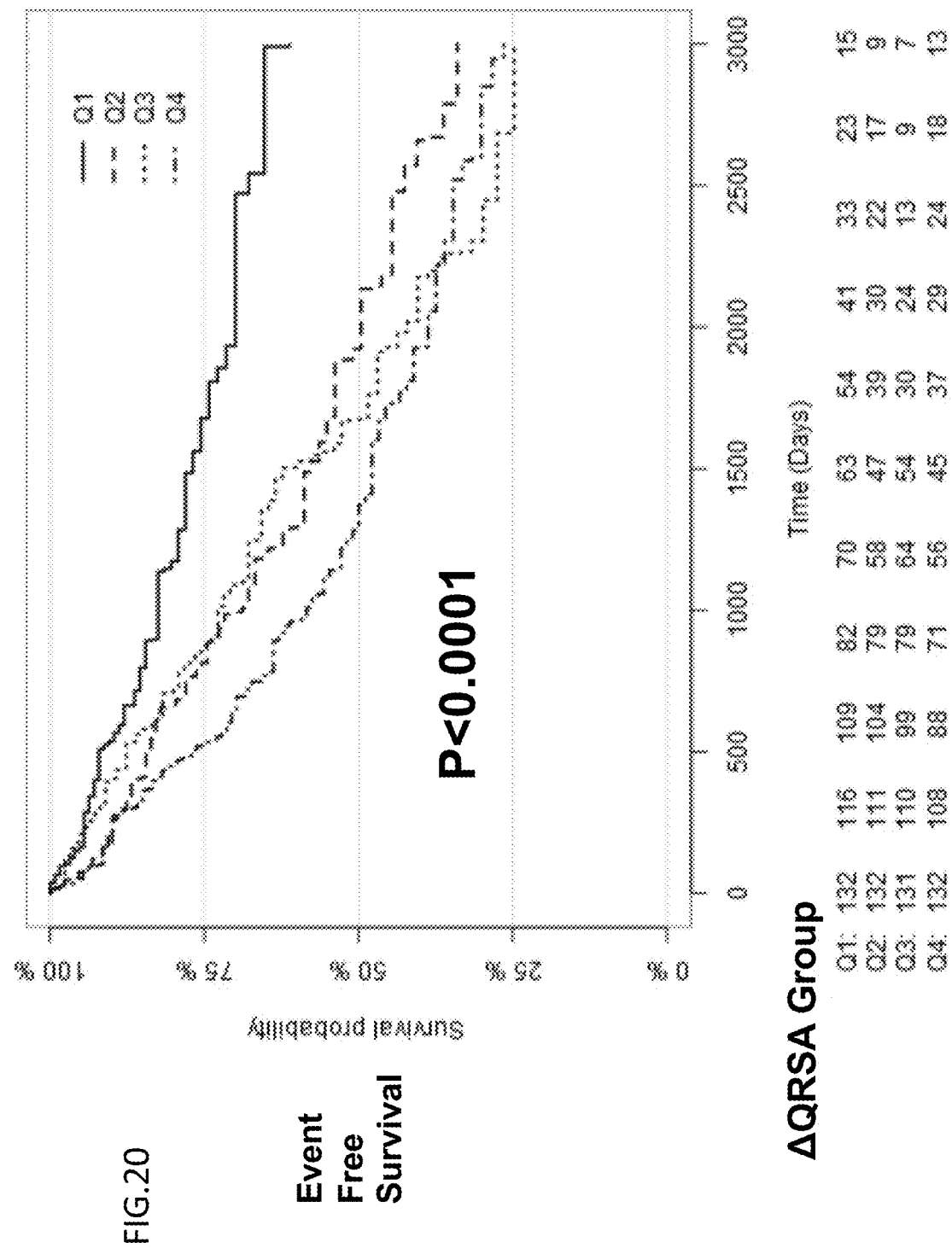

FIGS. 7 and 8 are X-ray images showing a chest area of a patient with a CRT device implanted therein;

FIG. 9 is a graph that visually depicts how QRS area is obtained using a vectorcardiogram (X, Y, and Z planes) in accordance with embodiments of the present disclosure;

FIG. 10 is a graph that visually depicts how the area of the Can to RV coil EGM can be obtained with and without pacing;

FIG. 11 are graphs showing EGM area measurements where the paced area is the same as the unpaced area;

FIG. 12 are graphs showing EGM area measurements where the paced area is less than the unpaced area;

FIG. 13 is a graph where the entire EGMA is measured including the portion generated by depolarization (corresponding to the ECG QRS area) and the portion generated by repolarization (corresponding to the ST segment and the entire QT interval);

FIG. 14 (identification of Selective His bundle capture) are graphs of EGM readings showing decrementing pulse amplitude pacing through a His bundle pacing lead paced from the V channel, EGM 1 is the atrial pacing channel, EGM 2 is the His bundle pacing channel, and EGM 3 is the Can to RV coil channel;

FIG. 15 are graphs of EGM readings showing decrementing pulse amplitude pacing through a His bundle pacing lead paced from the V channel;

FIG. 16 is a graph of EGM readings showing frequent PVCs occurring during biventricular pacing;

FIG. 17 is a flow chart of another exemplary method for determining an arrangement of electrodes of a CRT system with respect to a patient's heart in accordance with embodiments of the present disclosure;

FIG. 18 is a flow chart of another exemplary method for selecting CRT device electrodes, their electrical pulse amplitude and relative timing for application to a patient's heart in accordance with embodiments of the present disclosure;

FIG. 19 is a flow chart of another exemplary method for selecting CRT device electrodes and relative timing for application to a patient's heart in accordance with embodiments of the present disclosure; and FIG. 20 is a graph of a Kaplan Meier curve depicting the relationship between ΔQRSA quartile and incidence of LVAD, transplant, or death.

SUMMARY

The presently disclosed subject matter relates to systems and methods for selecting, positioning, and controlling CRT electrodes. According to an aspect, a CRT system includes one or more electrodes configured to be positioned on or in proximity to a subject's heart for receiving electrical signals carrying EGM data. The system also includes a CRT device operatively connected to the electrode(s). The CRT device is configured to receive the electrical signals from the electrode(s) when the one or more electrodes are positioned in a first arrangement with respect to the subject's heart. Further, the CRT device is configured to determine a second arrangement of the electrode(s) with respect to the subject's heart based on the carried EGM data. The CRT device is configured to present the second arrangement of the electrode(s).

According to another aspect, a CRT system includes one or more electrodes configured to be positioned on or in proximity to a subject's heart for receiving electrical signals carrying EGM data. The CRT system also includes a CRT device operatively connected to the electrode(s). The CRT device is configured to control the electrode(s) to apply electrical pulses to the subject's heart. Further, the CRT device is configured to receive the electrical signals from the electrode(s). The CRT device is also configured to select among the electrode(s) for applying a predetermined amplitude and timing of electrical pulses based on the EGM data. Further, the CRT device is configured to control the selected electrode(s) for applying the predetermined amplitude and timing of electrical pulses to the subject's heart.

DETAILED DESCRIPTION

The following detailed description is made with reference to the figures. Exemplary embodiments are described to illustrate the disclosure, not to limit its scope, which is defined by the claims. Those of ordinary skill in the art will recognize a number of equivalent variations in the description that follows.

Articles "a" and "an" are used herein to refer to one or to more than one (i.e. at least one) of the grammatical object of the article. By way of example, "an element" means at least one element and can include more than one element.

"About" is used to provide flexibility to a numerical endpoint by providing that a given value may be "slightly above" or "slightly below" the endpoint without affecting the desired result.

The use herein of the terms "including," "comprising," or "having," and variations thereof is meant to encompass the elements listed thereafter and equivalents thereof as well as additional elements. Embodiments recited as "including," "comprising," or "having" certain elements are also contemplated as "consisting essentially of" and "consisting" of those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a range is stated as between 1%-50%, it is intended that values such as between 2%-40%, 10%-30%, or 1%-3%, etc. are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary skill in the art to which this disclosure belongs.

As used herein, the terms "patient" and "subject" are used interchangeably and are intended to include human and non-human animals. Exemplary human subjects include a human patient in need of CRT, for example, patients having suffered a myocardial infarction, heart attack, and the like. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, and the like), and rodents (such as mice, rats, hamsters, guinea pigs, and the like).

As used herein, the term "data" may include, but is not limited to, any mechanical, electrical, ultrasound, magnetic signals, radiofrequency, the like, and combinations thereof that may be detected by the electrodes.

As used herein, the term "electrode" may refer to an electrical conductor used to make contact with a non-metallic component for sensing or detecting electrical signals. For example, electrodes disclosed herein may be positioned within veins or an organ (e.g., the heart) for sensing electrical signals. An electrode may be in electrical communication (e.g., via a wire) with a CRT device for communication of the sensed electrical signal to the CRT device.

As described herein, the systems and methods may comprise, consist of, or consist essentially of one or more pairs of reference electrodes and one or more pairs of pacing electrodes in electrical communication with a CRT device. The reference and pacing/sensing electrodes are configured to deliver and sense, respectively, small electrical, mechanical, ultrasound or magnetic signals delivered by the CRT device through the subject's body. In certain embodiments, the electrodes are implantable. Such electrodes may be unipolar or bipolar, and may be made of any suitable conducting material, such as, for example, stainless steel, ELGILOY® (a Co—Cr—Ni alloy), or MP35N alloy. The electrodes may be insulated with materials such as silicone rubber, polyurethane, or the like. In yet other embodiments, the reference electrodes may be placed on the body surface (e.g., such as a patch attached to a patient's chest or back). Such suitable reference electrodes include, but are not limited to, existing ENSITE/NAVX™ patches. These electrodes may be attached to leads (e.g., a lead may comprise one or more electrodes). The leads may be operatively connected to a CRT device, or function as independent satellite devices that are capable of communicating wirelessly (e.g., BLUETOOTH® wireless technology, WI-FI® wireless technology, or the like) with the CRT device.

Position tracking of the electrodes may be achieved in any of a variety of suitable manners to define a coordinate system (e.g., three-dimensional (3D) coordinate system) and to aid in acquisition of position and motion information for one or more implanted electrodes (e.g., due to cardiac mechanics). An implanted electrode may be positioned via a vessel (e.g., a vein) or via the pericardium (e.g., intrapericardial access to an epicardial location).

In other embodiments, the electrical information may be acquired as well and optionally used for gating acquisition of mechanical information or other purposes. Electrical activity may be measured using conventional techniques such as those for acquiring surface electrocardiograms or in vivo electrocardiograms. As described herein, the term "electrocardiogram" (EGM) includes surface electrocardiogram (ECG) and intracardiac electrogram (IEGM) as well as other types of electrograms that rely on one or more implanted electrodes.

Data that is collected may be analyzed with respect to stimulation energy delivered using one or more stimulation sites and/or one or more A-V intervals or V-V intervals. An analysis of such information may be used to determine an optimal pacing configuration. As used herein, the term "configuration" can account for more than electrode placement or location as one or more stimulation parameters and/or stimulation timings (e.g., interelectrode or intraelectrode timings) may be part of a "configuration."

An exemplary CRT device, also referred to herein as a "stimulation device," is described followed by various techniques for positioning the electrodes as well as acquiring and analyzing the data collected. In certain embodiments, the CRT device may comprise, consist of, or consist essentially of hardware, software, firmware, or combinations thereof configured to perform post-processing of information (e.g., mechanical, electrical, ultrasound, magnetic signals, or the like) and be configured for programming or operating an implantable device capable of delivering CRT. Example CRT devices include, but are not limited to, a pacemaker and a defibrillator.

Exemplary positions of the electrodes are provided below and are meant to be illustrative in nature only. It is recognized that one skilled in the art may make changes and/or modifications to the number of, or placement of such electrodes to achieve similar results. Such changes and/or modifications are within the scope of the present disclosure.

A number of different pacing/sensing electrode configurations are contemplated for use with the systems and methods of the present disclosure. For example, one or more pacing electrodes may be placed in the right ventricle along the intraventricular septum or apex and one or more pacing electrodes may be placed along the endocardial or epicardial surface of the left ventricle or in the region of the His bundle or other areas in or near the specialized conduction system. In accordance with embodiments of the present subject matter, FIG. 1 illustrates a diagram of an exemplary system including a CRT device 100 in electrical communication with a patient's heart 102 by way of various electrodes positioned for delivering heart stimulation and shock therapy in accordance with embodiments of the present disclosure. In such a configuration, a lead (e.g., a bipolar lead including an electrode) 104 can be positioned in the right ventricle 106. In accordance with embodiments, the lead 104 may be attached to the interventricular septum (not shown). A second lead 108 including one or more electrodes may be positioned through the coronary sinus to the posterior or lateral branch 110. A third lead 112 including one or more electrodes can be positioned through the coronary sinus to either a lateral or anterior branch 114, or via transseptal positioning to the LV endocardium, or left bundle area. Additionally, an anterior reference electrode 116 comprising one or more electrodes which may be positioned in the superior vena cava 118 for delivering multi-chamber stimulation and shock therapy. An unlimited number of total electrodes can be used and positioned along the septal, anterior, and lateral left ventricular walls to allow measurement of EGM area and CRT optimization by the systems and methods described herein. The leads 104, 108, 112, and 116 may be configurable for delivery of stimulation pulses suitable for stimulation of nerves or other tissue. Such leads may also include features such as bifurcations or legs. For example, a pacing lead as disclosed herein may include electrodes capable of delivering pacing pulses to a patient's left ventricle and one or more electrodes capable of stimulating an autonomic nerve. Further, the electrodes positioned in the proximal coronary sinus may function as an atrial pace/sensing electrode to time ventricular pacing. The proximal coronary sinus 107 is shown for reference.

FIG. 2 illustrates a block diagram depicting various example components of a CRT device 200 in accordance with embodiments of the present disclosure. While the diagram shown depicts a multi-chamber device, it is to be understood and appreciated that this is done for illustrative purposes only. Thus, the techniques, methods, and other examples described herein can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart.

A housing 202 for the CRT device 200 is often referred to as the "can," "case" or "case electrode," and may be programmably selected to act as the return electrode for all "unipolar" modes. The housing 202 may further be used as a return electrode alone or in combination with one or more of the coil electrodes for shocking or other purposes. The housing 202 may include a connector having a plurality of terminals 204, 206, 208, and 210 that are configured to connect the pacing/sensing leads (shown schematically, the number of connectors provided here is for illustrative purposes only). It is noted that one or more of the components of the CRT device 200 or any CRT device include the functionality described herein may be implemented by hardware, software, firmware, or combinations thereof.

The CRT device 200 is a programmable microcontroller 406 that controls the various modes of cardiac or other therapy. As is well known in the art, a microcontroller 212 typically includes a microprocessor, or equivalent control circuitry, designed specifically for controlling the delivery of stimulation therapy and monitoring/processing of mechanical information collected, and may further include RAM or ROM memory, logic and timing circuitry, state machine circuitry, and I/O circuitry. The microcontroller 212 can be configured to process or monitor input signals (data or information) as controlled by a program code stored in a designated block of memory. The type of microcontroller is not critical to the described implementations. Rather, any suitable microcontroller 212 may be used that is suitable to carry out the functions described herein. The use of microprocessor-based control circuits for performing timing and data analysis functions are well known in the art. Any suitable control circuitry may be used in connection with the described example and can include a microprocessor-based control system.

In addition to performing the traditional functions of a CRT device, the CRT device 200 can be capable of functioning as a traditional CRT pacemaker/defibrillator to treat both slow and fast arrhythmias with stimulation therapy, including but not limited to, cardioversion, defibrillation, and pacing stimulation 214. The microprocessor 212 may include an EGM area measurement module 216 configured to calculate the area contained within the entire or a portion of the EGM area from each connected lead. For example, the EGM area module 216 may be configured to calculate the area contained from an EGM obtained from a lead implanted in or on the epicardial surface of an atrium, ventricle, His bundle or other specialized conducting tissue, chest wall, intrathoracic vein, or other area. The microprocessor 212 may include a measurement module 218 configured to automatically measure and compare the EGM areas obtained from multiple pacing configurations and choose the configuration that produces the optimal calculated EGM area.

The microprocessor 212 may include a timing module 220 configured to control the timing of the stimulation pulses (e.g., pacing rate, atrio-ventricular (AV) delay, interatrial conduction (AA) delay, or interventricular conduction (VV) delay, pacing electrodes used for ventricular stimulation, and sequence of pacing electrode stimulation). Further, the timing module 220 can keep track of the timing of refractory periods, blanking intervals, noise detection windows, evoked response windows, alert intervals, marker channel timing, and the like. The timing module 220 may be configured to measure the EGM areas extrapolated from the averaged measurements obtained over several cardiac cycles in each pacing configuration.

The microprocessor 212 may include an assignment module 222 configured to automatically assign permanent or temporary pacing programming to the pacing configuration that optimizes the EGM area(s) obtained from one or multiple configurations.

The microprocessor 212 may include a re-measure module 224 configured to re-measure the EGM area(s) over several cardiac cycles in each pacing configuration in various physiological states (e.g., rest, mild exercise, peak exercise, or the like) to determine optimal pacing configurations for each physiological state. The CRT device 200 can subsequently re-measure the EGM area(s) over several cardiac cycles on a routine basis.

The microprocessor 212 may include an alarm module 226 configured to provide an auditory or sensory (e.g., vibration) alert to the patient and/or the medical provider if the EGM area exceeds a certain programmed threshold, indicative of inability to resynchronize the ventricle.

An electronic configuration switch 228 may include multiple switches for connecting the desired electrodes to the appropriate I/O circuits, thereby providing complete electrode programmability. Accordingly, the switch 228, in response to a control signal from the microcontroller 212, may determine the polarity of the stimulation pulses (e.g., unipolar, bipolar, or the like) by selectively closing the appropriate combination of switches (not shown) as is known in the art.

The microcontroller 212 may be communicatively connected to a memory 230 by a suitable data/address bus 232. The programmable operating parameters used by the microcontroller 212 may be stored and modified, as required, in order to customize the operation of the CRT device 200 to suit the needs of a particular patient. Such operating parameters may define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart within each respective tier of therapy. One feature of the described embodiments is the ability to sense and store a relatively large amount of data (e.g., from a data acquisition system). The data may subsequently be used for subsequent analysis to guide the programming of the device.

Advantageously, the operating parameters of the CRT device 200 may be non-invasively programmed into the memory 230 through a telemetry circuit in telemetric communication via communication link with an external device. Exemplary external devices include, but are not limited to, a programmer, transtelephonic transceiver, and a diagnostic system analyzer. The microcontroller 212 may activate the telemetry circuit with a control signal. The telemetry circuit allows EGMs and other information (e.g., status information relating to the operation of the device 200 or the like, as contained in the microcontroller 212 or memory 230) to be sent to an external device (not shown) through an established communication link.

The CRT device 200 may include a battery 234 configured to provide operating power to all of the circuits and/or component shown in FIG. 2. For the CRT device 200, which employs shocking therapy, the battery 234 can operate at low current drains for long periods of time (e.g., less than about 10 μA). Further, the battery 234 can provide high-current pulses (for capacitor charging) when the patient requires a shock pulse (e.g., in excess of about 2 Å, at voltages above 200 V, for periods of about 10 seconds or more). The battery 234 can have a predictable discharge characteristic so that elective replacement time can be detected.

The CRT device 200 can include magnet detection circuitry (not shown), coupled to the microprocessor 212, and configured to detect when a magnet is placed over the CRT device 200. The magnet may be used by a clinician to perform various test functions of the CRT device 200 and/or to signal the microprocessor 212 that the external programmer is in place to receive or transmit data to the microprocessor 212 through the telemetry circuits.

The CRT device 200 may include an impedance measuring circuit 236 that may be enabled by the microprocessor 212 via a control signal. Example functionality of the impedance measuring circuit 236 includes, but is not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, and the like. The impedance measuring circuit 236 may be coupled to the switch 228 so that any desired electrode may be used.

It is also within the scope of the present disclosure that the CRT device 200 may include one or more physiologic sensors (not shown). For example, the CRT device 200 may include a "rate-responsive" sensor that may provide, for example, information to aid in adjustment of pacing stimulation rate according to the state of the patient, such as diurnal changes in activity (e.g., detecting sleep and wake states). Accordingly, the microcontroller 212 may respond by adjusting the various pacing parameters (such as rate, A-V Delay, V-V Delay, etc.) at which stimulated pulses are generated.

It is to be understood that one or more physiologic sensors may also be external to the CRT device 200, yet still be implanted within or carried by the patient. Examples of physiologic sensors that may be implemented in the CRT device 200 include any suitable sensors that, for example, sense respiration rate, pH of blood, ventricular gradient, cardiac output, preload, afterload, contractility, and the like. Another sensor that may be used is one that detects activity variance, wherein an activity sensor is monitored diurnally to detect the low variance in the measurement corresponding to the sleep state.

The physiological sensor(s) may include sensors for detecting movement and minute ventilation in the patient. Signals generated by a position sensor, e.g., a MV sensor or the like, may be passed to the microprocessor 212 for analysis in determining whether to adjust the pacing rate, whether to reevaluate the EGM area and/or the like. The microprocessor 212 may monitor the signals for indications of the patient's position and activity status, such as whether the patient is climbing upstairs or descending downstairs or whether the patient is sitting up after lying down.

It is to be understood that the aforementioned components/modules may be implemented in hardware as part of the microprocessor 212, or as software/firmware instructions programmed into the device and executed on the microprocessor 212 during certain modes of operation. Alternatively, additional external devices, such as a CRT device programmer, may be connected to the CRT device to perform one or more of the above-described functions, or additional functions (e.g., provide additional memory/processing functions and the like). Such external devices may be in direct electrical communication or wireless (e.g., BLUETOOTH® wireless technology, WI-FI® wireless technology, or the like) with the implanted CRT device.

FIG. 3 illustrates a flow chart of an exemplary method for determining an arrangement of electrodes of a CRT system with respect to a patient's heart in accordance with embodiments of the present disclosure. The method is described by this example as being implemented by the CRT system shown in FIG. 1, although it should be understood that the method may alternatively be implemented by any suitable system.

Referring to FIG. 3, the method includes selecting 300 one or more implanted electrodes and one or more pairs of pacing/sensing electrodes in the thorax, heart and/or surrounding venous or subcutaneous structures of the patient (termed "arrangement" or "configuration"). For example, FIG. 1 shows the leads 104, 108, and 112 (including electrodes), and reference electrode 116 positioned on or in proximity to the heart 102. The electrodes may be in electrical communication with the CRT device 100. In embodiments, one or more pairs of reference electrodes may be positioned posterior to the left ventricle, and one or more pairs of reference electrodes may be positioned anterior of the right ventricle. In embodiments, the posterior reference electrodes may be positioned in the proximal azygos vein, the proximal coronary sinus, and at or near the bifurcation of the azygos and hemiazygos vein. In other embodiments, the anteriorly positioned reference electrodes may be positioned in the right ventricle, the superior vena cava, and at or near the CRT device, respectively. In other embodiments, electrodes may be positioned on these leads to provide the same or improved reference locations. In other embodiments, one or more pacing electrodes may be placed in the right ventricle along the intraventricular septum or apex, and one or more pacing electrodes may be placed along the endocardial or epicardial surface of the left ventricle. In embodiments, the one or more pacing electrodes may be positioned in the right ventricle, may be attached to the interventricular septum, one or more electrodes may be positioned through the coronary sinus to the posterior or lateral branch, and one or more electrodes may be positioned through the coronary sinus to either a lateral or anterior branch.

FIG. 3 includes receiving 302 electrical signals carrying EGM data from the electrodes. Continuing the aforementioned example, the CRT system 100 may receive electrical signals from the leads 104, 108, and 112 (including electrodes), and reference electrode 116 positioned as shown in FIG. 1. The electrical signals may be received over a period of time (e.g., one or more cardiac cycles). The electrical signals may carry EGM data as will be described in further detail herein. The EGM data may be stored in the CRT device 100. Alternatively, the EGM data may be stored in a computing device that is communicatively connected to the CRT device. For example, the CRT device 100 may be in communication with another computing device (e.g., laptop computer) via a wired or wireless connection.

The method of FIG. 3 includes assessing 304 another combination or arrangement of the electrodes within the patient's heart based on the EGM data. Continuing the aforementioned example, a processor in the CRT device 100 or one or more processors in a computing device that receives the EGM data may determine another arrangement for the leads 104, 108, and 112 (including electrodes) based on the EGM data. As an example, the other arrangement may be determined by calculating EGM area during CRT pacing and native conduction based on the received electrical signals; calculating the change in EGM area between CRT pacing and native conduction; and determining the second arrangement of the electrodes with respect to the patient's heart among multiple different arrangements such that the change in EGM area is optimized. In another example, the other arrangement may be determined by determining a baseline electrical dyssynchrony based on the carried EGM data; determining a risk of the patient having a cardiac episode based on the baseline electrical dyssynchrony; and determining the other arrangement of the electrodes based on an algorithm to reduce or eliminate the risk and to optimize the EGM area.

In yet another example of determining the other arrangement, the electrical signals may be received during CRT pacing of the patient's heart and during non His-bundle pacing of the electrodes. The electrical signals are received, in this example, during CRT pacing of the patient's heart by the CRT device and during His-bundle or conduction system pacing. The other arrangement may be determined by calculating EGM area, during CRT pacing and native conduction, based on the received electrical signals; calculating EGM area during the His-bundle or conduction system pacing; calculating the change in EGM area between native conduction; and determining, based on the change in EGM area, the other arrangement of the electrodes such that the change in EGM area is optimized.

The method of FIG. 3 includes presenting 306 the other arrangement of the electrodes. Continuing the aforementioned example, the CRT device 100 may use a suitable user interface to present information or instruction about arranging one or more of the leads 104, 108, and 112 (including electrodes), or electrodes placed in other arrangements including placement within the specialized conduction system in accordance with the assessing step 304. Based on experimentally determined values, a threshold change in EGM area will be determined that is associated with improved survival after CRT implantation. During CRT electrode implantation EGM area measurements made by the method described in FIG. 3 can be used to determine if any available CRT pacing configuration is capable of achieving the minimum needed change in EGM area to provide a high likelihood of CRT response. If no available pacing configuration produces the minimum threshold needed for CRT response, the device can alert the implanter through a warning on the external device programmer that the current electrode position is inadequate to achieve the desired procedural endpoint and that repositioning of the electrodes should be considered.

FIG. 4 illustrates a flow chart of an exemplary method for selecting CRT device electrodes and their electrical pulse amplitude and timing for application to a patient's heart in accordance with embodiments of the present disclosure. The method is described by this example as being implemented by the CRT system shown in FIG. 1, although it should be understood that the method may alternatively be implemented by any suitable system.

Referring to FIG. 4, the method includes positioning 400 one or more pairs of reference electrodes and one or more pairs of pacing/sensing electrodes in the thorax, heart and/or surrounding venous or subcutaneous structures of the patient (termed "arrangement" or "configuration"). For example, FIG. 1 shows the leads 104, 108, and 112 (including electrodes) positioned on or in proximity to the heart 102. The electrodes may be in electrical communication with the CRT device 100. Alternatively, the electrode may be positioned in any other suitable arrangement for applying electrical signals to the heart 102 and for receiving electrical signals.

FIG. 4 includes receiving 402 electrical signals carrying intracardiac EGM data from the electrodes. Continuing the aforementioned example, the CRT system 100 may receive electrical signals from the leads 104, 108, and 112 (including electrodes), as shown in FIG. 1. The electrical signals may be received over a period of time (e.g., one or more cardiac cycles). The electrical signals may carry EGM data as will be described in further detail herein. The EGM data may be stored in the CRT device 100. Alternatively, the EGM data may be stored in a computing device that is communicatively connected to the CRT device. For example, the CRT device 100 may be in communication with another computing device (e.g., laptop computer) via a wired or wireless connection.

The method of FIG. 4 includes selecting 404 among the electrodes for applying a predetermined amplitude and timing of electrical pulses based on the EGM data. Continuing the aforementioned example, a processor in the CRT device 100 or one or more processors in a computing device that receives the EGM data may select one or more of the leads 104, 108, and 112 (including electrodes), based on the EGM data. The CRT device 100 may select one or more electrodes among the available electrodes (e.g., electrodes of leads 104, 108, and 112), and may determine amplitude and electrical pulses (e.g., an electrical pulse pattern) for application by the selected electrode(s). For example, the CRT device may adjust the paced and/or sensed AV interval between 60 and 350 ms to optimize the change in EGM area. Additionally, the device may offset the timing of RV and LV stimulation in a biventricular pacing system to optimize EGM area. Additionally, in a biventricular CRT system with the capability to pace from ≥2 electrode configurations involving the LV lead ("multipoint pacing", the algorithm may identify that stimulation from 2 electrode configurations on the LV lead is required to optimize EGM area. Alternatively, in a biventricular CRT system, the CRT device may determine that LV only pacing synchronized to native conduction down the right bundle branch produces optimal change in EGM area and program the CRT device accordingly. In the setting of a His bundle or conduction system pacing CRT system, beat-to-beat optimization of the EGM area would allow the device to select a pacing amplitude that produces reliable capture of the conduction system without expending excess battery energy by maintaining output just above the capture threshold.

The method of FIG. 4 includes controlling 406 the selected electrode(s) for applying the predetermined amplitude and timing of electrical pulses to the patient's heart. Continuing the aforementioned example, the CRT device 100 may control the selected electrodes to apply the determined amplitude and timing of electrical pulses to the patient's heart 102. The device can use the EGM area to determine if pacing should be performed from the LV lead, the LV and RV lead, or neither. Further, the device may use the EGM area to determine the timing of stimulation from each electrode relative to the signal acquired from the atrial lead. In a His bundle or conduction system CRT system, the EGM area may be used to confirm reliable capture of the conduction system without burning excess battery capacity.

In experiments, it has been shown that 12-lead ECG derived vectorcardiographic (VCG) representations of ventricular activation may be useful for identifying an electrical substrate amendable to CRT. In these studies, a larger VCG derived QRS area (QRSA) on the baseline native conduction ECG was associated with increased likelihood of CRT response and more favorable long-term outcomes independent of QRS duration and morphology. These findings strongly suggest that QRSA is a robust non-invasive measure of LV activation delay. Based on these findings we sought to determine if non-invasive quantification of changes in LV activation, defined by absolute change in QRSA (ΔQRSA), can predict outcomes after CRT. Further, it was hypothesized that CRT induced reductions in QRSA may be associated with improved long-term outcomes.

In accordance with embodiments, change in QRSA can be used as a guide for positioning CRT device electrodes and for CRT device programming to optimize CRT and other cardiac-based therapies. The QRS area is a continuous variable that constitutes a vectorcardiographic (VCG) representation of ventricular depolarization. QRS area can be derived from a 12 lead ECG or other ECG configurations that are transformed into a VCG. The area under the curve (AUC) of the QRS complex in the X, Y, and Z component vectors can be used to calculate the total QRS area using the following formula: QRS area=$(QRSx^2+QRSy^2+QRSz^2)^{1/2}$. In a study of patients who underwent CRT implantation, tests were performed to determine if non-invasive quantification of changes in LV activation, defined by change (A) in QRS area (QRSA), can predict outcomes after CRT. CRT induced ΔQRSA was associated with clinically meaningful differences in event free survival, thus there was a continuous relationship between reduction in QRS area and outcomes.

CRT devices can measure ventricular depolarization via several device vectors including among others Can to RV coil, LV electrode to RV coil, and leadless ECG derived from microelectrodes located on the device Can. The vectors of these currently measured bipoles closely resemble VCG vector loops that are somewhat "off axis" relative to the true X, Y, and Z planes. It is part of test findings that the use of multiple device measured vectors allows for a detailed understanding of ventricular depolarization in a 3 dimensional space. For example, and as shown in FIGS. 7 and 8, the can to RV coil vector contains information from the X and Y planes while the LV to RV coil vector largely contains information in the Z plane.

FIG. 5 illustrates a graph showing the EGM area measured from the RV coil to Can EGM signal. The darker shaded area 500 indicates the positive component. The lighter shaded area 502 indicates the negative component. Total area is calculated as the sum of the absolute value of positive component 500 and the absolute value of the negative component 502.

FIG. 6 illustrates EGMs showing EGM area measured in the Can to RV coil EGM signal (middle tracing) and the LV electrode to RV coil configuration (bottom tracing). Referring to FIG. 6, the values from the multitude of measured vectors may be entered into an equation that weighs the value of each to derive the total EGM area.

By weighing the EGM areas obtained from each of these intracardiac EGM sources, the degree of baseline electrical dyssynchrony can be measured. Also, the effectiveness of electrical resynchronization provided by pacing therapy can be determined. Accordingly, one aspect of the present disclosure provides a method for optimizing CRT in a subject, the method comprising, consisting of, or consisting essentially of: (1) receiving electrical signals relating to ventricular depolarization from one or more standard pacing electrodes in typical anatomical positions and connected to a CRT device; (2) measuring and weighing the obtained EGM areas (EGMAs) from multiple electrode pairs during native conduction or non-CRT pacing to obtain a degree of baseline electrical dyssynchrony); (3); measuring and weighing the EGMAs obtained from multiple electrode pairs during CRT pacing to generate a ΔEGMA and (4) adjusting the programming of the CRT device to optimize the ΔEGMA. One of the key features to the present disclosure is the ability to continuously monitor the subject to allow for the continuous optimization of the therapy. Hence, in some embodiments, the method further comprises repeating steps (1)-(4) to reprogram the CRT device to continuously and maximally optimize the ΔEGMA.

Further, in accordance with embodiments, systems and methods provided herein can be used to augment/optimize the implantation of the electrodes to provide the optimal stimulation. Therefore, another aspect of the present disclosure provides a method of optimizing implantation of a CRT device, the method comprising, consisting of, or consisting essentially of: (1) receiving electrical signals relating to ventricular depolarization from one or more standard pacing electrodes in typical anatomical locations; (2) measuring and weighing the obtained EGMAs from multiple electrode pairs during native conduction or non CRT pacing to obtain a degree of baseline electrical dyssynchrony; (3) measuring and weighing the EGMAs obtained from each electrode during CRT pacing to generate a ΔEGMA; (4) repositioning the electrodes and repeating steps (1)-(4); (5) determining the optimal location of the electrodes based on the data received in steps (1)-(4); and (6) implanting a CRT device according to optimized electrode location.

The positioning (and repositioning of electrodes) as directed by the methods disclosed herein can be important to obtain the optimal therapy for the patient. In some embodiments, the one or more electrodes are positioned in a spot in the patient selected from the group consisting of a surface of a body, within a thorax of the body, a heart of the body, a surrounding venous structure of the body, and a surrounding subcutaneous structure of the body, and combinations thereof.

The systems and methods provided herein may also be used for assessing the risk of a patient having a cardiac episode, either at the time of implantation or later during the therapy. As used herein, the term "cardiac episode" refers to any cardiac event that can have a detrimental effect on the subject. In some embodiments, the cardiac episode is selected from the group consisting of a cardiac infarction, left ventricular dysfunction, heart failure, atrial arrhythmia, ventricular arrhythmia, and combinations thereof. Such cardiac episodes may result in changes in electrical conduction and ventricular size that result in measurable changes in EGMA that can be used to alert the patient and/or care provider that the patient is having said cardiac episode.

Another aspect of the present disclosure provides methods of assessing patient risk, the method comprising, consisting of, or consisting essentially of: (1) receiving electrical signals relating to ventricular depolarization from one or more electrodes from a cardiac device; (2) measuring and weighing the obtained EGMAs from multiple electrode pairs during native conduction or non CRT pacing to obtain a degree of baseline electrical dyssynchrony; (3) determining the short and long term risk of the patient having a cardiac episode; and (5) adjusting the programming of the cardiac device to optimize EGMA and reduce and/or eliminate the risk to the patient. In some embodiments, the method further comprises repeating steps (1)-(4) to continuously optimize the EGMA.

Another feature of the present disclosure allows one skilled in the art (e.g., a caregiver or other medical professional) to track the pacing of a subject's heart. Thus, the present disclosure further provides a method of tracking the pacing of a heart of a subject, the method comprising, consisting of, or consisting essentially of: (1) receiving electrical signals relating to ventricular depolarization from one or more electrodes from a cardiac device; (2) measuring and weighing the obtained EGMAs from multiple electrode pairs during CRT pacing to obtain a degree of electrical resynchronization or residual dyssynchrony; (3) matching the baseline electrical dyssynchrony to each beat of the heart; (4) optionally repeating steps (1)-(3); and (5) preparing a diagnostic readout for a medical provider to track the pacing of the subject's heart to differentiate fusion, pseudo-fusion, and fully paced beats. In some embodiments, the method further comprises adjusting the programming of the cardiac device to optimize ΔEGMA during each beat of the subject's heart.

Yet another aspect of the present disclosure provides a method of optimizing His Bundle or Conduction System pacing in a subject, the method comprising: (1) receiving electrical signals relating to ventricular depolarization from one or more electrodes from a cardiac device; (2) measuring and weighing the obtained EGMAs from multiple electrode pairs during native conduction or non His bundle or conduction system pacing (ventricular pacing) to obtain a degree of baseline electrical dyssynchrony; (3) measuring and weighing the EGMAs obtained from each electrode during His bundle or conduction system pacing to generate a ΔEGMA; (4) adjusting the programming of the cardiac device to optimize ΔEGMA, thereby ensuring His bundle or conduction system capture; and optionally (5) repeating steps (1)-(4) to reprogram the cardiac device to continuously optimize ΔEGMA the with the minimal needed battery output, continuously ensuring His bundle or conduction system or capture while maximizing CRT device battery longevity.

In some embodiments, a His-bundle or conduction system paced EGMA may be slightly greater or of the same magnitude as the intrinsic EGMA (i.e. narrow underlying EGM in a patient with insufficient atrioventricular conduction); in these cases, the device can be continuously adjusted to achieve the specified EGMA at a specified heart rate.

The present disclosure further provides systems and of using the provided herein for the optimization of CRT and other cardiac-based therapies. In one aspect, the system comprises, consists of, or consists essentially of: (1) one or more electrodes; and (2) a cardiac device, the cardiac device configured to (i) receiving electrical signals relating to ventricular depolarization from one or more standard pacing electrodes in typical anatomical locations; (ii) measuring and weighing the obtained EGMAs from multiple electrode pairs during native conduction or non CRT pacing to obtain a degree of baseline electrical dyssynchrony; (iii) measuring and weighing the EGMAs obtained from each electrode during CRT pacing to generate a ΔEGMA; (iv) repositioning the electrodes and repeating steps (i)-(iv); (v) determining the optimal location of the electrodes based on the data received in steps (i)-(iv); and (vi) implanting a CRT device according to optimized electrode location.

FIGS. 7 and 8 are X-ray images showing a chest area of a patient with a CRT device implanted therein. Referring to FIGS. 7 and 8, the measurement vectors of the RV coil to Can EGM (700), and LV electrode to RV coil EGM (702) are annotated. The RV coil to Can EGM vector roughly approximates the Y axis while the LV electrode to EV coil EGM roughly approximates the Z axis. Line 700 depicts RV to Can, which predominantly has X and Y plane data. Line 702 depicts RV to LV, which has X and Z plane data. Line 704 depicts LV to Can, which predominantly has Y and Z plane data. These lines are also shown in FIG. 1.

FIG. 9 is a graph that visually depicts how QRS area is obtained using a vectorcardiogram (X, Y, and Z planes) in accordance with embodiments of the present disclosure. This information was obtained from a 12 lead ECG. The formula shown at the bottom of FIG. 9 shows how QRS area can be calculated from the vectorcardiogram.

FIG. 10 is a graph that visually depicts how the area of the Can to RV coil EGM can be obtained with and without pacing. The Can to RV coil EGM areas is 1 of several areas that can be combined in a weighted equation to generate a global EGMA measurement during paced and unpaced states.

FIG. 11 are graphs showing EGM readings where the paced EGMA is the same as the unpaced EGMA (ΔEGMA=0), which may be a suboptimal pacing configuration for CRT. These readings suggest ineffective CRT delivery from this LV pacing location. As a result, the systems and methods disclosed herein may advise a different anatomic location for the CRT device electrodes or pacing from a different electrode in the current lead location or pacing with a different amplitude or timing to achieve more optimal ΔEGMA.

FIG. 12 are graphs showing EGM readings where the paced area is less than the unpaced area (ΔEGMA is a negative value, suggesting reduced LVAT), which may be a more optimal pacing configuration for CRT as compared to FIG. 11. These readings suggest CRT delivery from this LV pacing location with these pacing amplitudes and timing has changed ΔEGMA. If this ΔEGMA is optimal for reducing LVAT, the systems and methods disclosed herein may advise to use this positioning arrangement for the CRT device electrodes.

FIG. 13 shows a graph where the entire EGMA is measured including the portion generated by depolarization (corresponding to the ECG QRS area) and the portion generated by repolarization (corresponding to the ST segment and the entire QT interval). In this iteration measurement of the entire EGMA may be a simpler method for computation of the EGMA. Additionally, measurement of the entire EGMA may provide information corresponding to prolongation or alternans of the QT interval, and may predict impending episodes of ventricular tachycardia or fibrillation.

FIG. 14 are graphs of EGM readings showing decrementing pulse amplitude pacing through a His bundle pacing lead paced from the V, channel EGM 1 is the atrial pacing channel, EGM 2 is the His bundle pacing channel, and EGM 3 is the Can to RV coil channel. On the top line the stimulation to the evoked potential on EGM 2 is short, confirming His capture. On the bottom line the stimulation to EGM 2 is long, confirming loss of His capture. The EGM 2 and EGM 3 areas are identical during capture and loss of capture, confirming selective His bundle capture. Upon losing capture of the His bundle, (first beat, second row) there is no change in EGM or morphology compared to prior to loss of capture, confirming selective His bundle capture.

FIG. 15 are graphs of EGM readings showing decrementing pulse amplitude pacing through a His bundle pacing lead. This graph shows distinguishing Non-selective His bundle capture from peri-Hisian ventricular capture. EGM 1 is the atrial pacing channel, EGM 2 is the His bundle pacing channel, EGM 3 is the Can to RV coil channel. On the top line the stimulation to evoked potential on EGM 2 is short confirming capture. On the bottom line the first 3 beats demonstrate a short simulation to evoked potential on EGM 2 but a change in EGM 2 and EGM 3 morphology and increase in EGM 2 and EGM 3 area, consistent with loss of His bundle capture and development of peri-Hisian ventricular capture. Finally, on the last 2 pacing stimuli, there is no evoked potential on EGM 2, confirming loss of capture of both the His bundle and Peri-Hisian ventricle. This pattern is consistent with Non-selective capture from the His bundle pacing lead on the top line with small EGM 2 and EGM 3 areas, followed by loss of His bundle capture identified by increase in EGM 2 and EGM 3 areas, followed by complete loss of capture. Upon losing capture of the His bundle, (first beat, second row) there is a change in EGM area and morphology compared to prior to loss of capture, especially in EGM3, but there is still an evoked EGM. After the third beat there is no longer an EGM after the VP signal. This confirms that from 1V down to 0.5V the patient has Non-selective His bundle capture, followed by peri-Hisian ventricular capture, followed by lack of capture. The change in EGM3 area is able to identify loss of His bundle capture.

FIG. 16 is a graph of EGM readings showing frequent PVCs occurring during biventricular pacing. The EGM2 area is greater during PVCs than during biventricular paced beats suggesting that these PVCs produce worse dyssynchrony than biventricularly paced beats. Measuring the EGMA during PVCs and quantifying the PVC burden could provide important information on the likelihood that the PVCs may worsen LV function and HF symptoms. EGM 1 is the atrial channel, EGM 2 is the Can to RV coil EGM, and EGM 3 is the RV tip to RV ring EGM. The EGM 2 area increases during the third and seventh beats as a result of the electrical dyssynchrony produced by PVCs.

FIG. 17 illustrates a flow chart of another exemplary method for determining an arrangement of electrodes of a CRT system with respect to a patient's heart in accordance with embodiments of the present disclosure. Referring to FIG. 17, the method includes positioning 1700 right ventricular (RV) and left ventricular (LV) leads. The method also includes pacing 1702 in all available configurations or those manually selected by an operator and measuring EGM area in each configuration. Further, the method includes determining 1704 that no pacing configuration meets the change in EGMA threshold for likelihood of CRT response and subsequently the method proceeds to step 1700. For example, based on experimentally determined values, a threshold change in EGMA will be determined that is associated with improved survival after CRT implantation. During CRT electrode implantation EGMA measurements made by the method described in FIG. 3 will be used to determine if any available CRT pacing configuration is capable of achieving the optimal ΔEGMA required to provide a high likelihood of CRT response. If no available pacing configuration produces the ΔEGMA needed for CRT response, the device will alert the implanter through a warning on the external device programmer that the current electrode position is inadequate to achieve the desired procedural endpoint and that repositioning of the electrodes should be considered. Further, when determining 1706 that the device identifies an optimal pacing configuration that meets the ΔEGMA threshold for likelihood of CRT response, then the lead implant procedure is complete 1708 and this configuration can be utilized.

FIG. 18 illustrates a flow chart of another exemplary method for selecting CRT device electrodes and their electrical pulse amplitude and timing for application to a patient's heart in accordance with embodiments of the present disclosure. Referring to FIG. 18, the method includes periodically pacing 1800 from every ventricular configuration (including multipoint LV pacing configurations) or those manually selected by the operator with a range of AV and VV delays. The method also includes measuring 1802 EGMA in each configuration. Further, the method includes choosing 1804 the pacing configuration with the greatest ΔEGMA.

FIG. 19 illustrates a flow chart of another exemplary method for selecting CRT device electrodes and their electrical pulse amplitude and timing for application to a patient's heart in accordance with embodiments of the present disclosure. Referring to FIG. 19, the CRT device can implement the method and be used to determine heart rate (HR) of a patient. The method includes determining 1900 if the HR changes by 10 beats per minute (BPM) (or another suitable rate) and whether this last greater than 10 beats (or another suitable number of beats or time period). Further, the method includes determining 1900 whether the patient is physically active. In response to this determination at step 1900, the CRT device can pace for 1 beat from every available ventricular configuration (including multipoint LV pacing configurations) with a range of AV and VV delays.

The method of FIG. 19 includes using 1902 the CRT device to measure EGM area in each configuration. Further, the method includes using 1904 the CRT device to identify pacing configuration with optimal ΔEGMA within achievable heart rate ranges, reconfirm that finding, and programming that configuration into the CRT device for application to the patient. This allows for the determination of personalized and optimal CRT device programming in a heart rate specific manner.

FIG. 20 is a graph of a Kaplan Meier curve depicting the relationship between ΔQRSA quartile and incidence of LVAD, transplant, or death. Q1 had the greatest average reduction in QRSA, and Q4 had an average increase in QRSA.

EXPERIMENTS

In experiments, a retrospective analysis of patients who received a de novo CRT with defibrillator was performed. For this study, patients were required to have an LV ejection fraction (LVEF) of ≤35%, a QRS≥120 ms, and a digital ECG at baseline (≤180 days prior to CRT implantation) and ≤90 days after the index procedure. Patients were excluded if they died prior to discharge or if a follow-up ECG did not demonstrate evidence of CRT pacing. If multiple ECGs were available in the allowable pre- and/or post-CRT time frame the ECG closest to the procedure date was used.

Clinically obtained ECGs were reanalyzed in the GE MUSE Cardiology Information System version 8.0.2.10132 with analysis software version 241 (available from GE Healthcare, Chicago, Ill.) and exported in XML format. QRS morphology was designated by two readers blinded to outcome. Left bundle branch block (LBBB) morphology was further divided into strict and non-strict LBBB using the Strauss criteria. Notably, the Strauss criteria incorporate information on both QRS duration and characteristics (e.g., notching). QRS onset and offset and thereby QRS duration as detected by the software were over read and manually corrected if needed.

VCGs were derived from the XML files using customized MATLAB software (MathWorks, Inc., Natick, Mass.) using the Kors matrices based on previous data suggesting VCGs resulting from the Kors transformation were more predictive of outcomes after CRT compared to Inverse Dower transformed VCGs. QRSA was calculated for each pre- and post-CRT ECG using the median complex. The area under the depolarization curve was calculated for each of the 3 planes (X,Y,Z). The 3-dimensional QRSA was calculated as $(QRSx^2+QRSy^2+QRSz^2)^{1/2}$. The absolute CRT induced change in QRS area (ΔQRSA) was calculated as post-CRT QRSA minus pre-CRT QRSA; with this convention, a negative value represents a reduction in LV activation time which was hypothesized to represent a favorable prognostic sign. In contrast, a ΔQRSA>0 (i.e., a positive value) would represent an overall increase in LV activation time which was hypothesized to identify increased risk for adverse outcomes.

Baseline characteristics of the overall study population and after stratification by quartile of ΔQRSA were described using proportions for categorical variables and medians and interquartile ranges for continuous variables. The first ΔQRSA quartile was defined as the quartile with the most negative ΔQRSA (greatest decrease in QRSA with CRT), the 4th ΔQRSA quartile was defined as the quartile with the most positive ΔQRSA (smallest decrease or increase in QRSA with CRT), and the $2^{nd}$ and $3^{rd}$ quartiles represented intermediate groups. Differences between groups were tested using the Chi-square test for categorical variables and Wilcoxon Rank Sum test for continuous variables.

The unadjusted long term association between ΔQRSA quartile and time until transplant, LVAD, or death, was visually depicted using a Kaplan Meier plot and differences were assessed using the Log Rank test. The adjusted long term association between ΔQRSA quartile and time until transplant, LVAD, or death, was assessed using Cox proportional hazards models with Q4 as the reference group. Adjustment variables included age, sex, atrial fibrillation or flutter, ischemic heart disease, ejection fraction, QRS morphology, beta blocker use, and ACEi or ARB use. Interactions between model variables were assessed, and there were no significant interactions using a p<0.01 (an a priori decision due to multiplicity of testing). The association between ΔQRSA (across the continuous range) and outcomes was assessed using an adjusted restricted cubic spline with 3 knots with a ΔQRSA of 0 being assigned a hazard ratio of 1. Statistical analysis was performed in RStudio version 1.1447 (RStudio, Inc, Boston, Mass., USA) running R version 3.4.4 (R Foundation for Statistical Computing, Vienna, Austria). A p<0.05 was considered statistically significant except during interaction testing (to account for multiple testing).

A total of 1001 patients underwent CRT-D implant during the study period. After excluding patients with missing ECG (n=407), QRS duration<120 ms (n=39), LVEF>35% (n=18), death prior to discharge (n=7), and non-CRT paced QRS morphology on the follow-up ECG (n=1), or poor quality follow-up ECG (n=2) a total of 527 patients were available for analysis. The overall study population was older (67.7 years, IQR 57.6-75.2), predominantly male (70%), and demonstrated a severely reduced ejection fraction (25.0%, IQR 20.0-30.0) with advanced HF symptoms (81.2% NYHA III symptom class). Medical comorbidities were common, including ischemic cardiomyopathy (54.1%), hypertension (71.5%), diabetes (38.3%), and atrial fibrillation or flutter (34.2%). LBBB was present in 64.2% of patients and the median QRS duration was 160 ms (IQR 144-180).

The median baseline QRSA of the overall population was 93.6 µVs (IQR 61.3-127.3) and this decreased to 59.7 µVs (IQR 41.7-82.8) with CRT pacing (P<0.0001). After the overall population was stratified by quartile of ΔQRSA, the heterogeneity in ΔQRSA across the population became evident. Patients with the most negative ΔQRSA (largest reduction in LV activation delay) were more commonly female, had non-ischemic cardiomyopathy, a longer baseline QRS duration, a strict LBBB, and a larger baseline QRSA. Patients with a smaller reduction (or even increase) in QRSA with CRT more commonly had atrial fibrillation or flutter, chronic lung disease, a prior ICD, or treatment with amiodarone.

ΔQRSA (by quartile) was strongly associated with incident LVAD, transplant, or death in an unadjusted Log Rank analysis. Examination of the Kaplan Meier curve demonstrates that greater reductions in QRSA were associated with increasingly favorable long term outcomes across study quartiles. An adjusted Cox proportional hazards model (with Q4 as the reference group) demonstrated that ΔQRSA was significantly associated with outcomes; although the point estimate suggested that Q1, Q2, and Q3, all had more favorable outcomes compared to Q4, the only difference reaching statistical significance was the Q1 vs. Q4 comparison. There were no statistical interactions between baseline QRS morphology, ΔQRSA, and outcome. An adjusted spline analysis demonstrated that the relationship between ΔQRSA and incident LVAD, transplant, or death was preserved across the continuous range and that no threshold value was evident.

In further experiments a retrospective analysis was performed in the same CRT patient dataset to determine if there is a correlation between QRSA and EGMA. CRT device interrogation reports containing both BIV paced and native conducted EGM complexes were saved in digital format. Reports were manually reviewed to confirm that the recorded EGM signals contained the can to RV coil recording. Investigators manually measured the area contained within the recorded can to RV coil EGM. The area contained within the positive and negative deflections were recorded separately and the absolute values were combined to calculate the total EGMA occurring in the first 120 ms of ventricular activation. The can to RV coil EGM areas measured during native conduction were correlated with ECG QRS area calculated by Kors transformation during native conduction as described previously. The can to RV coil EGM areas measured during BIV CRT pacing were correlated with ECG QRS area calculated by Kors transformation during BIV CRT pacing. EGM+area, EGM−area, and EGM total area were all correlated separately.

A total of 21 patients were analyzed. There was a correlation between the positive EGM deflection area during native conduction obtained in the can to RV coil configuration and native conduction ECG QRSA by the Kors transformation ($R^2=0.50$, p=0.0005). There was also a positive correlation between the total EGMA occurring in the first 120 ms of ventricular depolarization and the native conduction ECG QRSA by the Kors transformation ($R^2=0.41$, p=0.002). Correlations also existed between the native conduction positive EGMA and total EGMA and change in QRSA ($R^2=0.36$ p=0.0055 and $R^2=0.30$ p=0.0126, respectively) and between the BIV paced positive EGMA, total EGMA and negative EGMA and change in QRSA ($R^2=0.37$ p=0.005, $R^2=0.47$ p=0.0009, and $R^2=0.44$ p=0.002, respectively).

The functional units described in this specification have been labeled as computing devices. A computing device may be implemented in programmable hardware devices such as processors, digital signal processors, central processing units, field programmable gate arrays, programmable array logic, programmable logic devices, cloud processing systems, or the like. The computing devices may also be implemented in software for execution by various types of processors. An identified device may include executable code and may, for instance, comprise one or more physical or logical blocks of computer instructions, which may, for instance, be organized as an object, procedure, function, or other construct. Nevertheless, the executable of an identified device need not be physically located together but may comprise disparate instructions stored in different locations which, when joined logically together, comprise the computing device and achieve the stated purpose of the computing device. In another example, a computing device may be a mobile computing device such as, for example, but not limited to, a smart phone, a cell phone, a pager, a personal digital assistant (PDA), a mobile computer with a smart phone client, or the like. In another example, a computing device may be any type of wearable computer, such as a computer with a head-mounted display (HMD), or a smart watch or some other wearable smart device. A computing device can also include any type of conventional computer, for example, a laptop computer or a tablet computer. A typical mobile computing device is a wireless data access-enabled device (e.g., an iPHONE® smart phone, a BLACKBERRY® smart phone, a NEXUS ONE™ smart phone, an iPAD® device, smart watch, or the like) that is capable of sending and receiving data in a wireless manner using protocols like the Internet Protocol, or IP, and the wireless application protocol, or WAP. This allows users to access information via wireless devices, such as smart watches, smart phones, mobile phones, pagers, two-way radios, communicators, and the like. Wireless data access is supported by many wireless networks, including, but not limited to, Bluetooth, Near Field Communication, CDPD, CDMA, GSM, PDC, PHS, TDMA, FLEX, ReFLEX, iDEN, TETRA, DECT, DataTAC, Mobitex, EDGE and other 2G, 3G, 4G, 5G, and LTE technologies, and it operates with many handheld device operating systems, such as PalmOS, EPOC, Windows CE, FLEXOS, OS/9, JavaOS, iOS and Android. Typically, these devices use graphical displays and can access the Internet (or other communications network) on so-called mini- or micro-browsers, which are web browsers with small file sizes that can accommodate the reduced memory constraints of wireless networks. In a representative embodiment, the mobile device is a cellular telephone or smart phone or smart watch that operates over GPRS (General Packet Radio Services), which is a data technology for GSM networks or operates over Near Field Communication e.g. Bluetooth. In addition to a conventional voice communication, a given mobile device can communicate with another such device via many different types of message transfer techniques, including Bluetooth, Near Field Communication, SMS (short message service), enhanced SMS (EMS), multi-media message (MMS), email WAP, paging, or other known or later-developed wireless data formats. Although many of the examples provided herein are implemented on smart phones, the examples may similarly be implemented on any suitable computing device, such as a computer.

An executable code of a computing device may be a single instruction, or many instructions, and may even be distributed over several different code segments, among different applications, and across several memory devices. Similarly, operational data may be identified and illustrated herein within the computing device, and may be embodied in any suitable form and organized within any suitable type of data structure. The operational data may be collected as a single data set, or may be distributed over different locations including over different storage devices, and may exist, at least partially, as electronic signals on a system or network.

The described features, structures, or characteristics may be combined in any suitable manner in one or more embodiments. In the following description, numerous specific details are provided, to provide a thorough understanding of embodiments of the disclosed subject matter. One skilled in the relevant art will recognize, however, that the disclosed subject matter can be practiced without one or more of the specific details, or with other methods, components, materials, etc. In other instances, well-known structures, materials, or operations are not shown or described in detail to avoid obscuring aspects of the disclosed subject matter.

As used herein, the term "memory" is generally a storage device of a computing device. Examples include, but are not limited to, read-only memory (ROM) and random access memory (RAM).

The device or system for performing one or more operations on a memory of a computing device may be a software, hardware, firmware, or combination of these. The device or the system is further intended to include or otherwise cover all software or computer programs capable of performing the various heretofore-disclosed determinations, calculations, or the like for the disclosed purposes. For example, exemplary embodiments are intended to cover all software or computer programs capable of enabling processors to implement the disclosed processes. Exemplary embodiments are also intended to cover any and all currently known, related art or later developed non-transitory recording or storage mediums (such as a CD-ROM, DVD-ROM, hard drive, RAM, ROM, floppy disc, magnetic tape cassette, etc.) that record or store such software or computer programs. Exemplary embodiments are further intended to cover such software, computer programs, systems and/or processes provided through any other currently known, related art, or later developed medium (such as transitory mediums, carrier waves, etc.), usable for implementing the exemplary operations disclosed below.

In accordance with the exemplary embodiments, the disclosed computer programs can be executed in many exemplary ways, such as an application that is resident in the memory of a device or as a hosted application that is being executed on a server and communicating with the device application or browser via a number of standard protocols, such as TCP/IP, HTTP, XML, SOAP, REST, JSON and other sufficient protocols. The disclosed computer programs can be written in exemplary programming languages that execute from memory on the device or from a hosted server, such as BASIC, COBOL, C, C++, Java, Pascal, or scripting languages such as JavaScript, Python, Ruby, PHP, Perl, or other suitable programming languages.

As referred to herein, the terms "computing device" and "entities" should be broadly construed and should be understood to be interchangeable. They may include any type of computing device, for example, a server, a desktop computer, a laptop computer, a smart phone, a cell phone, a pager, a personal digital assistant (PDA, e.g., with GPRS NIC), a mobile computer with a smartphone client, or the like.

As referred to herein, a user interface is generally a system by which users interact with a computing device. A user interface can include an input for allowing users to manipulate a computing device, and can include an output for allowing the system to present information and/or data, indicate the effects of the user's manipulation, etc. An example of a user interface on a computing device (e.g., a mobile device) includes a graphical user interface (GUI) that allows users to interact with programs in more ways than typing. A GUI typically can offer display objects, and visual indicators, as opposed to text-based interfaces, typed command labels or text navigation to represent information and actions available to a user. For example, an interface can be a display window or display object, which is selectable by a user of a mobile device for interaction. A user interface can include an input for allowing users to manipulate a computing device, and can include an output for allowing the computing device to present information and/or data, indicate the effects of the user's manipulation, etc. An example of a user interface on a computing device includes a graphical user interface (GUI) that allows users to interact with programs or applications in more ways than typing. A GUI typically can offer display objects, and visual indicators, as opposed to text-based interfaces, typed command labels or text navigation to represent information and actions available to a user. For example, a user interface can be a display window or display object, which is selectable by a user of a computing device for interaction. The display object can be displayed on a display screen of a computing device and can be selected by and interacted with by a user using the user interface. In an example, the display of the computing device can be a touch screen, which can display the display icon. The user can depress the area of the display screen where the display icon is displayed for selecting the display icon. In another example, the user can use any other suitable user interface of a computing device, such as a keypad, to select the display icon or display object. For example, the user can use a track ball or arrow keys for moving a cursor to highlight and select the display object.

The display object can be displayed on a display screen of a mobile device and can be selected by and interacted with by a user using the interface. In an example, the display of the mobile device can be a touch screen, which can display the display icon. The user can depress the area of the display screen at which the display icon is displayed for selecting the display icon. In another example, the user can use any other suitable interface of a mobile device, such as a keypad, to select the display icon or display object. For example, the user can use a track ball or times program instructions thereon for causing a processor to carry out aspects of the present disclosure.

As referred to herein, a computer network may be any group of computing systems, devices, or equipment that are linked together. Examples include, but are not limited to, local area networks (LANs) and wide area networks (WANs). A network may be categorized based on its design model, topology, or architecture. In an example, a network may be characterized as having a hierarchical internetworking model, which divides the network into three layers: access layer, distribution layer, and core layer. The access layer focuses on connecting client nodes, such as workstations to the network. The distribution layer manages routing, filtering, and quality-of-server (QoS) policies. The core layer can provide high-speed, highly-redundant forwarding services to move packets between distribution layer devices in different regions of the network. The core layer typically includes multiple routers and switches.

The present subject matter may be a system, a method, and/or a computer program product. The computer program product may include a computer readable storage medium (or media) having computer readable program instructions thereon for causing a processor to carry out aspects of the present subject matter.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a RAM, a ROM, an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network, or Near Field Communication. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present subject matter may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++, Javascript or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present subject matter.

Aspects of the present subject matter are described herein with reference to flowchart illustrations and/or block diagrams of methods, apparatus (systems), and computer program products according to embodiments of the subject matter. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present subject matter. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the embodiments have been described in connection with the various embodiments of the various figures, it is to be understood that other similar embodiments may be used, or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed is:

1. A cardiac resynchronization therapy (CRT) system comprising:
   electrodes configured to be positioned on or in proximity to a subject's heart for receiving electrical signals carrying EGM data; and
   a CRT device operatively connected to the electrodes, and the CRT device being configured to:
      receive the electrical signals from the electrodes when the electrodes are positioned in a first arrangement with respect to the subject's heart, wherein the electrical signals are received during CRT pacing of the subject's heart by the CRT device and during native conduction of the electrodes;
      calculate EGM area (EGMA) during CRT pacing and native conduction based on the received electrical signals;
      calculate the change in EGMA (ΔEGMA) between CRT pacing and native conduction;
      determine a second arrangement of the electrodes with respect to the subject's heart based on the EGMA and among a plurality of different arrangements such that the ΔEGMA is optimized to improve patient outcomes; and
      present the second arrangement of the electrodes.

2. The CRT system of claim 1, wherein the CRT device is one of an implantable CRT device, a pacemaker, and a defibrillator.

3. The CRT system of claim 1, wherein the electrodes are configured to be positioned on one or more of a surface of a body of a subject, within a thorax of the body, on a heart of the body, on a surrounding venous structure of the body, and/or on a surrounding subcutaneous structure of the body.

4. The CRT system of claim 1, wherein the electrical signals are received during CRT pacing of the subject's heart by the CRT device.

5. A cardiac resynchronization therapy (CRT) system comprising:
   electrodes configured to be positioned on or in proximity to a subject's heart for receiving electrical signals carrying EGM data wherein the carried EGM data is associated with ventricular depolarization from the electrodes; and
   a CRT device operatively connected to the electrodes, and the CRT device being configured to:
      receive the electrical signals from the electrodes when the electrodes are positioned in a first arrangement with respect to the subject's heart;
      calculate EGM area (EGMA) based on the received electrical signals;
      determine a baseline electrical dyssynchrony based on the carried EGM data;
      determine a risk of the subject having a cardiac episode based on the baseline electrical dyssynchrony;
      determine a second arrangement of the electrodes with respect to the subject's heart based on the EGMA and based on an algorithm to reduce or eliminate the risk and to optimize EGMA; and
      present the second arrangement of the electrodes.

6. A cardiac resynchronization therapy (CRT) system comprising:
   electrodes configured to be positioned on or in proximity to a subject's heart for receiving electrical signals carrying EGM data; and
   a CRT device operatively connected to the electrodes, and the CRT device being configured to:
      receive the electrical signals from the electrodes when the electrodes are positioned in a first arrangement with respect to the subject's heart, wherein the electrical signals are received during CRT pacing of the subject's heart by the CRT device and during non His-bundle pacing of the electrodes, and wherein electrical signal are received during CRT pacing of the subject's heart by the CRT device and during His-bundle pacing,
      calculate the EGM area (EGMA) during CRT pacing and native conduction based on the received electrical signals;
      calculate EGMA during the His-bundle or conduction system pacing;
      calculate the change in EGMA (ΔEGMA) between native conduction; and
      determine, based on the ΔEGMA, a second arrangement of the electrodes with respect to the subject's heart based on the EGMA such that the ΔEGMA is optimized; and
      present the second arrangement of the electrodes.

7. A method comprising:
   positioning electrodes of a cardiac resynchronization therapy (CRT) device on or in proximity to a subject's heart for receiving electrical signals carrying EGM data;
   receiving the electrical signals from the electrodes when the electrodes are positioned in a first arrangement with respect to the subject's heart;
   receiving the electrical signals during CRT pacing of the subject's heart by the CRT device and during native conduction of the electrodes;
   calculating, during CRT pacing and native conduction, EGM area (EGMA) based on the received electrical signals;
   calculating the change in EGMA (ΔEGMA) between CRT pacing and native conduction;
   determining a second arrangement of the electrodes with respect to the subject's heart based on the EGMA and among a plurality of different arrangements such that the ΔEGMA is optimized; and
   presenting the second arrangement of the electrodes.

8. The method of claim 7, further comprising positioning the electrodes on one or more of a surface of a body of a subject, within a thorax of the body, on a heart of the body, on a surrounding venous structure of the body, and on a surrounding subcutaneous structure of the body.

9. The method of claim 7, further comprising receiving the electrical signals during CRT pacing of the subject's heart by the CRT device.

10. A method comprising:
    positioning electrodes of a cardiac resynchronization therapy (CRT) device on or in subject's heart for receiving electrical signals carrying EGM data, wherein the carried EGM data is associated with ventricular depolarization from the electrodes;
    receiving the electrical signals from the electrodes when the electrodes are positioned in a first arrangement with respect to the subject's heart;

calculating EGM area (EGMA) based on the received electrical signals;

determining a baseline electrical dyssynchrony based on the carried EGM data;

determining a risk of the subject having a cardiac episode based on the baseline electrical dyssynchrony; and determining a second arrangement of the electrodes with respect to the subject's heart and based on the EGMA based on an algorithm to reduce or eliminate the risk and to optimize EGMA; and presenting the second arrangement of the electrodes.

11. The method of claim 7, wherein the CRT device is one of an implantable CRT device, a pacemaker, and a defibrillator.

* * * * *

UNITED STATES PATENT AND TRADEMARK OFFICE
CERTIFICATE OF CORRECTION

PATENT NO. : 11,511,118 B2
APPLICATION NO. : 16/786975
DATED : November 29, 2022
INVENTOR(S) : Brett Atwater and Daniel Friedman Page 1 of 1

It is certified that error appears in the above-identified patent and that said Letters Patent is hereby corrected as shown below:

In the Claims

At Claim 10, Column 26, Line 62, please replace the phrase with:
-- therapy (CRT) device on or in proximity to a subject's heart for --

Signed and Sealed this
Twenty-fifth Day of July, 2023

Katherine Kelly Vidal
*Director of the United States Patent and Trademark Office*